United States Patent
Baumbach et al.

(10) Patent No.: US 12,403,296 B2
(45) Date of Patent: Sep. 2, 2025

(54) APPARATUS FOR ANCHORING A VENTRICULAR ASSIST SYSTEM IN A BLOOD VESSEL, OPERATING METHOD, PRODUCTION METHOD FOR PRODUCING AN APPARATUS AND VENTRICULAR ASSIST SYSTEM

(71) Applicant: KARDION GMBH, Stuttgart (DE)

(72) Inventors: Hardy Baumbach, Stuttgart (DE); Armin Schuelke, Aidlingen (DE); Inga Schellenberg, Stuttgart (DE); David Minzenmay, Stuttgart (DE)

(73) Assignee: KARDION GMBH, Stuttgart (DE)

( * ) Notice: Subject to any disclaimer, the term of this patent is extended or adjusted under 35 U.S.C. 154(b) by 1252 days.

(21) Appl. No.: 17/057,420

(22) PCT Filed: May 30, 2019

(86) PCT No.: PCT/EP2019/064158
§ 371 (c)(1),
(2) Date: Jun. 1, 2021

(87) PCT Pub. No.: WO2019/229224
PCT Pub. Date: Dec. 5, 2019

(65) Prior Publication Data
US 2021/0290931 A1    Sep. 23, 2021

(30) Foreign Application Priority Data
May 30, 2018 (DE) ............... 10 2018 208 555.2

(51) Int. Cl.
*A61M 60/165* (2021.01)
*A61M 60/148* (2021.01)
(Continued)

(52) U.S. Cl.
CPC ........ *A61M 60/165* (2021.01); *A61M 60/148* (2021.01); *A61M 60/178* (2021.01);
(Continued)

(58) Field of Classification Search
CPC .............. A61M 60/148; A61M 60/165; A61M 60/216; A61F 2/2466; A61F 2002/2484; A61F 2/2427; A61F 2/243
See application file for complete search history.

(56) References Cited

U.S. PATENT DOCUMENTS

| 2,254,698 A | 9/1941 | Hansen, Jr. |
| 3,085,407 A | 4/1963 | Tomlinson |

(Continued)

FOREIGN PATENT DOCUMENTS

| CA | 3 000 581 | 4/2017 | |
| CA | 3000581 A1 * | 4/2017 | ............ A61M 60/13 |

(Continued)

OTHER PUBLICATIONS

International Preliminary Report on Patentability and Written Opinion received in PCT Application No. PCT/EP2019/064158, dated Oct. 8, 2020 in 18 pages.

(Continued)

*Primary Examiner* — Seema Mathew
(74) *Attorney, Agent, or Firm* — Knobbe, Martens, Olson & Bear, LLP

(57) ABSTRACT

The invention relates to an apparatus (100) for anchoring a ventricular assist system in a blood vessel, the apparatus (100) being able to assume an insertion state for insertion of the ventricular assist system into the blood vessel, and the apparatus (100) being able to assume an anchoring state in order to anchor the ventricular assist system in the blood vessel. The apparatus (100) has at least one fixing means (105) for fixing the apparatus (100) to the ventricular assist (Continued)

system (205), a crown (110) and a connection means (115). The crown (110) is formed from at least one unfolding element (120). The unfolding element (120) is designed to unfold during the transfer from the insertion state into the anchoring state in order to enlarge the diameter of the crown (110) so as to anchor the apparatus (100) in the blood vessel. The connection means (115) is designed to connect the crown (110) to the fixing means (105).

10 Claims, 16 Drawing Sheets

(51) Int. Cl.
*A61M 60/178* (2021.01)
*A61M 60/183* (2021.01)
*A61M 60/216* (2021.01)
*A61M 60/861* (2021.01)

(52) U.S. Cl.
CPC ........ *A61M 60/183* (2021.01); *A61M 60/216* (2021.01); *A61M 60/861* (2021.01); *A61M 2205/0266* (2013.01)

(56) References Cited

U.S. PATENT DOCUMENTS

| | | | |
|---|---|---|---|
| 3,568,659 | A | 3/1971 | Karnegis |
| 3,614,181 | A | 10/1971 | Meeks |
| 3,645,268 | A | 2/1972 | Capote |
| 3,747,998 | A | 7/1973 | Klein et al. |
| 3,790,878 | A | 2/1974 | Brokaw |
| 3,807,813 | A | 4/1974 | Milligan |
| 4,441,210 | A | 4/1984 | Hochmair et al. |
| 4,522,194 | A | 6/1985 | Normann |
| 4,802,650 | A | 2/1989 | Stricker |
| 4,888,009 | A | 12/1989 | Lederman et al. |
| 4,888,011 | A | 12/1989 | Kung et al. |
| 4,896,754 | A | 1/1990 | Carlson et al. |
| 4,902,272 | A | 2/1990 | Milder et al. |
| 4,919,647 | A | 4/1990 | Nash |
| 4,943,275 | A | 7/1990 | Stricker |
| 4,968,300 | A | 11/1990 | Moutafis et al. |
| 4,985,014 | A | 1/1991 | Orejola |
| 5,000,177 | A | 3/1991 | Hoffmann et al. |
| 5,061,256 | A | 10/1991 | Wampler |
| 5,084,064 | A | 1/1992 | Barak et al. |
| 5,090,957 | A | 2/1992 | Moutafis et al. |
| 5,112,292 | A | 5/1992 | Hwang et al. |
| 5,116,305 | A | 5/1992 | Milder et al. |
| 5,195,877 | A | 3/1993 | Kletschka |
| 5,289,821 | A | 3/1994 | Swartz |
| 5,322,509 | A | 6/1994 | Rickerd |
| 5,330,460 | A | 7/1994 | Moss et al. |
| 5,354,271 | A | 10/1994 | Voda |
| 5,409,463 | A | 4/1995 | Thomas et al. |
| 5,443,503 | A | 8/1995 | Yamane |
| 5,599,173 | A | 2/1997 | Chen et al. |
| 5,613,935 | A | 3/1997 | Jarvik |
| 5,629,661 | A | 5/1997 | Ooi et al. |
| 5,647,127 | A | 7/1997 | Miyata et al. |
| 5,690,674 | A | 11/1997 | Diaz |
| 5,702,430 | A | 12/1997 | Larson, Jr. et al. |
| 5,713,954 | A | 2/1998 | Rosenberg et al. |
| 5,752,937 | A | 5/1998 | Otten et al. |
| 5,766,207 | A | 6/1998 | Potter et al. |
| 5,814,900 | A | 9/1998 | Esser |
| 5,843,141 | A | 12/1998 | Bischoff et al. |
| 5,888,242 | A | 3/1999 | Antaki et al. |
| 5,921,913 | A | 7/1999 | Siess |
| 5,928,132 | A | 7/1999 | Leschinsky |
| 5,982,153 | A | 11/1999 | Nagal |
| 6,053,873 | A | 4/2000 | Govari et al. |
| 6,058,958 | A | 5/2000 | Benkowski et al. |
| 6,149,405 | A | 11/2000 | Abe et al. |
| 6,152,909 | A | 11/2000 | Bagaoisan |
| 6,159,198 | A | 12/2000 | Gardeski et al. |
| 6,176,848 | B1 | 1/2001 | Rau et al. |
| 6,212,430 | B1 | 4/2001 | Kung et al. |
| 6,224,540 | B1 | 5/2001 | Lederman et al. |
| 6,254,359 | B1 | 7/2001 | Aber |
| 6,264,601 | B1 | 7/2001 | Jassawalla et al. |
| 6,324,430 | B1 | 11/2001 | Zarinetchi et al. |
| 6,324,431 | B1 | 11/2001 | Zarinetchi et al. |
| 6,361,292 | B1 | 3/2002 | Chang et al. |
| 6,366,817 | B1 | 4/2002 | Kung |
| 6,389,318 | B1 | 5/2002 | Zarinetchi et al. |
| 6,398,734 | B1 | 6/2002 | Cimochowski et al. |
| 6,400,991 | B1 | 6/2002 | Kung |
| 6,442,434 | B1 | 8/2002 | Zarinetchi et al. |
| 6,445,956 | B1 | 9/2002 | Laird et al. |
| 6,450,948 | B1 | 9/2002 | Matsuura et al. |
| 6,471,713 | B1 | 10/2002 | Vargas et al. |
| 6,496,733 | B2 | 12/2002 | Zarinetchi et al. |
| 6,497,681 | B1 | 12/2002 | Brenner |
| 6,508,756 | B1 | 1/2003 | Kung et al. |
| 6,516,227 | B1 | 2/2003 | Meadows et al. |
| 6,527,698 | B1 | 3/2003 | Kung et al. |
| 6,530,876 | B1 | 3/2003 | Spence |
| 6,540,658 | B1 | 4/2003 | Fasciano et al. |
| 6,544,247 | B1 | 4/2003 | Gardeski et al. |
| 6,553,263 | B1 | 4/2003 | Meadows et al. |
| 6,561,975 | B1 | 5/2003 | Pool et al. |
| 6,592,620 | B1 | 7/2003 | Lancisi et al. |
| 6,743,239 | B1 | 6/2004 | Kuehn |
| 6,794,789 | B2 | 9/2004 | Siess et al. |
| 6,879,126 | B2 | 4/2005 | Paden et al. |
| 6,979,338 | B1 | 12/2005 | Loshakove et al. |
| 7,022,100 | B1 | 4/2006 | Aboul-Hosn et al. |
| 7,062,331 | B2 | 6/2006 | Zarinetchi et al. |
| 7,070,398 | B2 | 7/2006 | Olsen et al. |
| 7,155,291 | B2 | 12/2006 | Zarinetchi et al. |
| 7,160,243 | B2 | 1/2007 | Medvedev |
| 7,166,088 | B2 | 1/2007 | Heuser |
| 7,241,257 | B1 | 7/2007 | Ainsworth et al. |
| 7,250,041 | B2 | 7/2007 | Chiu et al. |
| 7,338,521 | B2 | 3/2008 | Antaki et al. |
| 7,357,794 | B2 | 4/2008 | Makower et al. |
| 7,419,486 | B2 | 9/2008 | Kampa |
| 7,513,864 | B2 | 4/2009 | Kantrowitz et al. |
| 7,520,850 | B2 | 4/2009 | Brockway |
| 7,621,894 | B2 | 11/2009 | Leeflang et al. |
| 7,722,568 | B2 | 5/2010 | Lenker et al. |
| 7,744,571 | B2 | 6/2010 | Fisher et al. |
| 7,762,941 | B2 | 7/2010 | Jarvik |
| 7,794,384 | B2 | 9/2010 | Sugiura et al. |
| 7,819,916 | B2 | 10/2010 | Yaegashi |
| 7,824,375 | B2 | 11/2010 | Hastings, Jr. et al. |
| 7,841,976 | B2 | 11/2010 | McBride et al. |
| 7,878,967 | B1 | 2/2011 | Khanal |
| 7,942,805 | B2 | 5/2011 | Shambaugh, Jr. |
| 7,951,119 | B2 | 5/2011 | Leeflang et al. |
| 7,959,551 | B2 | 6/2011 | Jarvik |
| 8,012,079 | B2 | 9/2011 | Delgado, III |
| 8,025,647 | B2 | 9/2011 | Siess et al. |
| 8,043,263 | B2 | 10/2011 | Helgeson et al. |
| 8,075,472 | B2 | 12/2011 | Zilbershlag et al. |
| 8,088,059 | B2 | 1/2012 | Jarvik |
| 8,088,154 | B2 | 1/2012 | Hoffman et al. |
| 8,152,845 | B2 | 4/2012 | Bourque |
| 8,157,719 | B1 | 4/2012 | Ainsworth et al. |
| 8,231,519 | B2 | 7/2012 | Reichenbach et al. |
| 8,262,619 | B2 | 9/2012 | Chebator et al. |
| 8,292,908 | B2 | 10/2012 | Nieman et al. |
| 8,343,028 | B2 | 1/2013 | Gregoric et al. |
| 8,382,830 | B2 | 2/2013 | Maher et al. |
| 8,461,817 | B2 | 6/2013 | Martin et al. |
| 8,475,431 | B2 | 7/2013 | Howat |
| 8,480,627 | B2 | 7/2013 | Christiansen |
| 8,485,961 | B2 | 7/2013 | Campbell et al. |
| 8,489,200 | B2 | 7/2013 | Zarinetchi et al. |
| 8,545,380 | B2 | 10/2013 | Farnan et al. |
| 8,579,966 | B2 | 11/2013 | Seguin et al. |

(56) References Cited

U.S. PATENT DOCUMENTS

| | | | |
|---|---|---|---|
| 8,591,538 B2 | 11/2013 | Gellman | |
| 8,591,539 B2 | 11/2013 | Gellman | |
| 8,597,170 B2 | 12/2013 | Walters et al. | |
| 8,608,635 B2 | 12/2013 | Yomtov et al. | |
| 8,612,002 B2 | 12/2013 | Faltys et al. | |
| 8,613,777 B2 | 12/2013 | Siess et al. | |
| 8,620,447 B2 | 12/2013 | D'Ambrosio et al. | |
| 8,684,904 B2 | 4/2014 | Campbell et al. | |
| 8,721,517 B2 | 5/2014 | Zeng et al. | |
| 8,727,959 B2 | 5/2014 | Reitan et al. | |
| 8,728,055 B2 | 5/2014 | Stehr et al. | |
| 8,734,331 B2 | 5/2014 | Evans et al. | |
| 8,766,788 B2 | 7/2014 | D'Ambrosio | |
| 8,814,776 B2 | 8/2014 | Hastie et al. | |
| 8,827,890 B2 | 9/2014 | Lee et al. | |
| 8,852,173 B2 | 10/2014 | Sigg et al. | |
| 8,862,232 B2 | 10/2014 | Zarinetchi et al. | |
| 8,870,739 B2 | 10/2014 | LaRose et al. | |
| 8,888,728 B2 | 11/2014 | Aboul-Hosn et al. | |
| 8,900,114 B2 | 12/2014 | Tansley et al. | |
| 8,900,115 B2 | 12/2014 | Bolling et al. | |
| 8,926,564 B2 | 1/2015 | King et al. | |
| 8,932,246 B2 | 1/2015 | Ferrari | |
| 8,961,389 B2 | 2/2015 | Zilbershlag | |
| 8,992,406 B2 | 3/2015 | Corbett | |
| 9,002,468 B2 | 4/2015 | Shea et al. | |
| 9,002,469 B2 | 4/2015 | D'Ambrosio | |
| 9,071,182 B2 | 6/2015 | Yoshida et al. | |
| 9,138,518 B2 | 9/2015 | Campbell et al. | |
| 9,144,669 B2 | 9/2015 | Wieselthaler | |
| 9,149,606 B2 | 10/2015 | Beissel et al. | |
| 9,162,017 B2 | 10/2015 | Evans et al. | |
| 9,168,060 B2 | 10/2015 | Voss | |
| 9,220,826 B2 | 12/2015 | D'Ambrosio | |
| 9,283,314 B2 | 3/2016 | Prasad et al. | |
| 9,308,305 B2 | 4/2016 | Chen et al. | |
| 9,327,068 B2 | 5/2016 | Aboul-Hosn et al. | |
| 9,364,592 B2 * | 6/2016 | McBride | F04D 29/528 |
| 9,381,286 B2 | 7/2016 | Spence et al. | |
| 9,402,942 B2 | 8/2016 | Hastie et al. | |
| 9,427,509 B2 | 8/2016 | Vodermayer | |
| 9,440,013 B2 | 9/2016 | Dowling et al. | |
| 9,452,249 B2 | 9/2016 | Kearsley et al. | |
| 9,456,898 B2 | 10/2016 | Barnes et al. | |
| 9,486,566 B2 | 11/2016 | Siess | |
| 9,492,600 B2 | 11/2016 | Strueber et al. | |
| 9,510,813 B2 | 12/2016 | Levy et al. | |
| 9,539,094 B2 | 1/2017 | Dale et al. | |
| 9,539,378 B2 | 1/2017 | Tuseth | |
| 9,545,468 B2 | 1/2017 | Aboul-Hosn et al. | |
| 9,561,314 B2 | 2/2017 | Aboul-Hosn et al. | |
| 9,561,362 B2 | 2/2017 | Malinowski | |
| 9,569,985 B2 | 2/2017 | Alkhatib et al. | |
| 9,585,991 B2 | 3/2017 | Spence | |
| 9,592,397 B2 | 3/2017 | Hansen et al. | |
| 9,597,063 B2 | 3/2017 | Voss et al. | |
| 9,603,984 B2 | 3/2017 | Romero et al. | |
| 9,616,107 B2 | 4/2017 | VanAntwerp et al. | |
| 9,616,159 B2 | 4/2017 | Anderson et al. | |
| 9,656,011 B2 | 5/2017 | Graham et al. | |
| 9,669,144 B2 | 6/2017 | Spanier et al. | |
| 9,682,180 B2 | 6/2017 | Hoarau et al. | |
| 9,713,701 B2 | 7/2017 | Sarkar et al. | |
| 9,717,831 B2 | 8/2017 | Schuermann | |
| 9,724,083 B2 | 8/2017 | Quadri et al. | |
| 9,744,279 B2 | 8/2017 | Tamez et al. | |
| 9,750,861 B2 | 9/2017 | Hastie et al. | |
| 9,769,912 B2 | 9/2017 | Helm et al. | |
| 9,782,905 B2 | 10/2017 | Drake et al. | |
| 9,789,238 B2 | 10/2017 | Aboul-Hosn et al. | |
| 9,800,172 B1 | 10/2017 | Leabman | |
| 9,807,860 B2 | 10/2017 | Helm et al. | |
| 9,814,813 B2 | 11/2017 | Corbett | |
| 9,814,814 B2 | 11/2017 | Corbett et al. | |
| 9,821,101 B2 | 11/2017 | Andrus et al. | |
| 9,821,146 B2 | 11/2017 | Tao et al. | |
| 9,827,356 B2 | 11/2017 | Muller et al. | |
| 9,833,314 B2 | 12/2017 | Corbett | |
| 9,833,611 B2 | 12/2017 | Govea et al. | |
| 9,848,899 B2 | 12/2017 | Sliwa et al. | |
| 9,872,948 B2 | 1/2018 | Siess | |
| 9,974,893 B2 | 5/2018 | Toellner | |
| 9,974,894 B2 | 5/2018 | Morello | |
| 9,974,938 B2 | 5/2018 | Pepin et al. | |
| 9,999,714 B2 | 6/2018 | Spanier et al. | |
| 10,010,412 B2 * | 7/2018 | Taft | A61F 2/95 |
| 10,080,871 B2 | 9/2018 | Schumacher et al. | |
| 10,123,875 B2 | 11/2018 | Wildhirt et al. | |
| 10,143,571 B2 | 12/2018 | Spence et al. | |
| 10,148,126 B2 | 12/2018 | Hoarau | |
| 10,183,104 B2 | 1/2019 | Anderson et al. | |
| 10,207,037 B2 | 2/2019 | Corbett et al. | |
| 10,207,038 B2 | 2/2019 | Neumann | |
| 10,238,782 B2 | 3/2019 | Barry | |
| 10,238,783 B2 | 3/2019 | Aboul-Hosn et al. | |
| 10,258,771 B2 | 4/2019 | Beissel et al. | |
| 10,279,093 B2 | 5/2019 | Reichenbach et al. | |
| 10,300,185 B2 | 5/2019 | Aboul-Hosn et al. | |
| 10,300,249 B2 | 5/2019 | Tao et al. | |
| 10,350,384 B2 | 7/2019 | Farnan et al. | |
| 10,357,598 B2 | 7/2019 | Aboul-Hosn et al. | |
| 10,376,162 B2 | 8/2019 | Edelman et al. | |
| 10,441,771 B2 | 10/2019 | Bickhart et al. | |
| 10,449,279 B2 | 10/2019 | Muller | |
| 10,463,508 B2 | 11/2019 | Spence et al. | |
| 10,478,542 B2 | 11/2019 | Jahangir | |
| 10,493,191 B2 | 12/2019 | Whisenant et al. | |
| 10,537,431 B2 | 1/2020 | Zhou et al. | |
| 10,537,672 B2 | 1/2020 | Tuseth et al. | |
| 10,576,192 B2 | 3/2020 | Muller et al. | |
| 10,576,258 B2 | 3/2020 | Fantuzzi et al. | |
| 10,617,808 B2 | 4/2020 | Hastie et al. | |
| 10,709,828 B2 | 7/2020 | Toellner et al. | |
| 10,732,583 B2 | 8/2020 | Rudser | |
| 10,737,008 B2 | 8/2020 | Corbett et al. | |
| 10,737,086 B2 | 8/2020 | Agrawal et al. | |
| 10,806,904 B2 | 10/2020 | Jelle et al. | |
| 10,864,015 B2 | 12/2020 | Von Segesser | |
| 10,864,308 B2 | 12/2020 | Muller et al. | |
| 10,881,836 B2 | 1/2021 | Schumacher et al. | |
| 10,881,845 B2 | 1/2021 | Siess et al. | |
| 10,894,143 B2 | 1/2021 | Yokoyama | |
| 10,898,625 B2 | 1/2021 | Toellner | |
| 10,944,293 B2 | 3/2021 | Nakao | |
| 10,953,205 B2 | 3/2021 | Korkuch | |
| 10,959,878 B2 | 3/2021 | Wolfertz et al. | |
| 10,967,152 B2 | 4/2021 | Korkuch | |
| 11,000,282 B2 | 5/2021 | Schuelke et al. | |
| 11,007,350 B2 | 5/2021 | Tao et al. | |
| 11,045,624 B2 | 6/2021 | Oiwa | |
| 11,045,634 B2 | 6/2021 | Korkuch et al. | |
| 11,056,878 B2 | 7/2021 | Gao et al. | |
| 11,058,851 B2 | 7/2021 | Farnan | |
| 11,065,417 B2 | 7/2021 | Inukai et al. | |
| 11,065,437 B2 | 7/2021 | Aber et al. | |
| 11,071,857 B2 | 7/2021 | Sun | |
| 11,076,884 B2 | 8/2021 | Anderson et al. | |
| 11,090,465 B2 | 8/2021 | Weber et al. | |
| 11,096,568 B2 | 8/2021 | Harrah et al. | |
| 11,103,715 B2 | 8/2021 | Fort | |
| 11,110,265 B2 | 9/2021 | Johnson | |
| 11,121,580 B2 | 9/2021 | Partovi | |
| 11,129,959 B2 | 9/2021 | Hart et al. | |
| 11,129,969 B2 | 9/2021 | Pederson, Jr. et al. | |
| 11,173,295 B2 | 11/2021 | Mack et al. | |
| 11,179,559 B2 | 11/2021 | Hansen | |
| 11,191,927 B2 | 12/2021 | McLaughlin et al. | |
| 11,197,690 B2 | 12/2021 | Fantuzzi et al. | |
| 11,219,755 B2 | 1/2022 | Siess et al. | |
| 11,224,737 B2 | 1/2022 | Petersen et al. | |
| 11,241,312 B2 | 2/2022 | Simonin | |
| 11,266,502 B1 * | 3/2022 | Wallace | A61F 2/2442 |
| 11,291,800 B2 | 4/2022 | Yokota | |
| 11,291,805 B2 | 4/2022 | Ouchi et al. | |

(56) References Cited

U.S. PATENT DOCUMENTS

| | | |
|---|---|---|
| 11,291,821 B2 | 4/2022 | Agrawal et al. |
| 11,291,826 B2 | 4/2022 | Tuval et al. |
| 11,291,855 B2 | 4/2022 | Wiesener |
| 11,304,747 B2 | 4/2022 | Simani et al. |
| 11,304,755 B2 | 4/2022 | Cao et al. |
| 11,311,311 B2 | 4/2022 | Sperry et al. |
| 11,316,371 B1 | 4/2022 | Partovi et al. |
| 11,317,988 B2 | 5/2022 | Hansen et al. |
| 11,318,284 B2 | 5/2022 | Ishida et al. |
| 11,318,285 B2 | 5/2022 | Ishida |
| 11,318,290 B2 | 5/2022 | Kleinhaus |
| 11,324,920 B2 | 5/2022 | Inukai et al. |
| 11,331,082 B2 | 5/2022 | Itoh et al. |
| 11,331,450 B2 | 5/2022 | Sakaguchi |
| 11,331,451 B2 | 5/2022 | Yamashita et al. |
| 11,344,717 B2 | 5/2022 | Kallenbach et al. |
| 11,351,359 B2 | 6/2022 | Clifton et al. |
| 11,351,360 B2 | 6/2022 | Rudser et al. |
| 11,364,363 B2 | 6/2022 | Fantuzzi et al. |
| 11,368,081 B2 | 6/2022 | Vogt et al. |
| 11,369,413 B2 | 6/2022 | Murphy |
| 11,369,785 B2 | 6/2022 | Callaway et al. |
| 11,369,786 B2 | 6/2022 | Menon et al. |
| 11,377,512 B2 | 7/2022 | Kuramoto et al. |
| 11,389,633 B2 | 7/2022 | Rohl et al. |
| 11,389,641 B2 | 7/2022 | Nguyen et al. |
| 11,400,261 B2 | 8/2022 | Mathews et al. |
| 11,406,395 B2 | 8/2022 | Wada et al. |
| 11,406,483 B2 | 8/2022 | Wirbisky et al. |
| 11,406,520 B2 | 8/2022 | Lam |
| 11,406,522 B2 | 8/2022 | Folan et al. |
| 11,406,798 B2 | 8/2022 | Kambara |
| 11,406,799 B2 | 8/2022 | McEvaddy et al. |
| 11,406,802 B2 | 8/2022 | DeGraaf et al. |
| 11,413,443 B2 | 8/2022 | Hodges et al. |
| 11,413,444 B2 | 8/2022 | Nix et al. |
| 11,413,446 B2 | 8/2022 | Siess et al. |
| 11,419,721 B2 | 8/2022 | Poppe et al. |
| 11,419,743 B2 | 8/2022 | Poppe et al. |
| 11,426,562 B2 | 8/2022 | Fantuzzi |
| 11,439,791 B2 | 9/2022 | Ishida |
| 11,439,806 B2 | 9/2022 | Kimball et al. |
| 11,446,044 B2 | 9/2022 | Bonnette et al. |
| 11,446,414 B2 | 9/2022 | Oiwa |
| 11,452,575 B2 | 9/2022 | Morey et al. |
| 11,458,285 B2 | 10/2022 | Graham et al. |
| 11,471,026 B2 | 10/2022 | Piskun et al. |
| 11,471,663 B2 | 10/2022 | Tuval et al. |
| 11,471,665 B2 | 10/2022 | Clifton et al. |
| 11,471,692 B2 | 10/2022 | Aghassian et al. |
| 11,484,698 B2 | 11/2022 | Radman |
| 11,497,889 B2 | 11/2022 | Mixter et al. |
| 11,497,894 B2 | 11/2022 | Korkuch et al. |
| 11,497,896 B2 | 11/2022 | Tanner et al. |
| 11,497,906 B2 | 11/2022 | Grace et al. |
| 11,503,993 B2 | 11/2022 | Chu et al. |
| 11,504,102 B2 | 11/2022 | Stanton et al. |
| 11,511,083 B2 | 11/2022 | Wada |
| 11,511,084 B2 | 11/2022 | Chu |
| 11,511,098 B2 | 11/2022 | Agrawal et al. |
| 11,511,101 B2 | 11/2022 | Hastie et al. |
| 11,517,191 B2 | 12/2022 | Oskin |
| 11,517,720 B2 | 12/2022 | Korkuch et al. |
| 11,517,737 B2 | 12/2022 | Struthers et al. |
| 11,517,738 B2 | 12/2022 | Wisniewski |
| 11,517,740 B2 | 12/2022 | Agarwa et al. |
| 11,523,905 B2 | 12/2022 | Griswold et al. |
| 11,524,137 B2 | 12/2022 | Jahangir |
| 11,529,508 B2 | 12/2022 | Jablonsk et al. |
| 11,529,510 B2 | 12/2022 | Leven |
| 11,540,857 B2 | 1/2023 | Olson et al. |
| 11,564,710 B2 | 1/2023 | Fitterer et al. |
| 11,565,093 B2 | 1/2023 | Kirt et al. |
| 11,583,670 B2 | 2/2023 | Pfeifer et al. |
| 11,583,671 B2 | 2/2023 | Nguyen et al. |
| 11,596,727 B2 | 3/2023 | Siess et al. |
| 11,602,448 B2 | 3/2023 | Nygaard et al. |
| 11,602,624 B2 | 3/2023 | Siess et al. |
| 11,616,397 B2 | 3/2023 | Schilling |
| 11,628,280 B2 | 4/2023 | Schumacher et al. |
| 11,633,574 B2 | 4/2023 | Watanabe |
| 11,642,511 B2 | 5/2023 | Delgado, III |
| 11,642,512 B2 | 5/2023 | Schilling |
| 11,660,434 B2 | 5/2023 | Korkuch et al. |
| 11,682,924 B2 | 6/2023 | Hansen et al. |
| 11,689,057 B2 | 6/2023 | Hansen |
| 11,690,606 B2 | 7/2023 | Muller et al. |
| 11,690,979 B2 | 7/2023 | Voss et al. |
| 11,690,997 B2 | 7/2023 | Georges et al. |
| 11,697,002 B2 | 7/2023 | Korkuch |
| 11,699,551 B2 | 7/2023 | Diekhans et al. |
| 11,730,939 B2 | 8/2023 | Siess et al. |
| 11,730,942 B2 | 8/2023 | Fantuzzi et al. |
| D998,799 S | 9/2023 | Okamura et al. |
| 11,744,567 B2 | 9/2023 | Deuel et al. |
| 11,744,638 B2 | 9/2023 | Davies et al. |
| 11,745,005 B2 | 9/2023 | Delgado, III |
| 11,751,751 B2 | 9/2023 | Calabrese et al. |
| 11,751,753 B2 | 9/2023 | Levasseur et al. |
| 11,752,308 B2 | 9/2023 | Tao et al. |
| 11,752,354 B2 | 9/2023 | Stotz et al. |
| 11,759,610 B2 | 9/2023 | Calabrese et al. |
| 11,766,264 B2 | 9/2023 | Phan et al. |
| 11,766,555 B2 | 9/2023 | Matthes et al. |
| 11,771,444 B2 | 10/2023 | Crawford et al. |
| 11,779,194 B2 | 10/2023 | Wilder et al. |
| 11,779,338 B2 | 10/2023 | Gordon et al. |
| 11,779,361 B2 | 10/2023 | Kugler et al. |
| 11,779,729 B2 | 10/2023 | Guimaraes et al. |
| 11,779,743 B2 | 10/2023 | Agrawal et al. |
| 11,786,109 B2 | 10/2023 | Golden et al. |
| 11,786,701 B2 | 10/2023 | Maki et al. |
| 11,786,720 B2 | 10/2023 | Muller |
| 11,793,530 B2 | 10/2023 | Chu et al. |
| 11,793,977 B2 | 10/2023 | Korkuch et al. |
| 11,804,767 B2 | 10/2023 | Vogt et al. |
| 11,806,046 B2 | 11/2023 | Fantuzzi et al. |
| 11,806,116 B2 | 11/2023 | Tuval et al. |
| 11,806,117 B2 | 11/2023 | Tuval et al. |
| 11,806,258 B2 | 11/2023 | Hingston et al. |
| 11,812,944 B2 | 11/2023 | Wales et al. |
| 11,812,951 B2 | 11/2023 | Mitelberg et al. |
| 11,812,952 B2 | 11/2023 | Abbott et al. |
| 11,813,183 B2 | 11/2023 | Christakis et al. |
| 11,826,517 B2 | 11/2023 | Fuller et al. |
| 11,832,793 B2 | 12/2023 | McWeeney et al. |
| 11,832,868 B2 | 12/2023 | Smail et al. |
| 11,833,314 B2 | 12/2023 | Corbett et al. |
| 11,833,316 B2 | 12/2023 | Hayakawa et al. |
| 11,833,342 B2 | 12/2023 | Tanner et al. |
| 11,844,592 B2 | 12/2023 | Tuval et al. |
| 11,844,909 B2 | 12/2023 | Tassoni et al. |
| 11,844,940 B2 | 12/2023 | D'Ambrosio et al. |
| 11,850,373 B2 | 12/2023 | Golden et al. |
| 11,857,159 B2 | 1/2024 | Saenz Villalobos et al. |
| 11,857,161 B2 | 1/2024 | Nguyen et al. |
| 11,857,197 B2 | 1/2024 | Alexander et al. |
| 11,857,740 B2 | 1/2024 | Chu |
| 11,857,743 B2 | 1/2024 | Fantuzzi et al. |
| 11,864,746 B2 | 1/2024 | Melilli et al. |
| 11,865,275 B2 | 1/2024 | O'Carrol et al. |
| 11,871,962 B2 | 1/2024 | Tehrani et al. |
| 11,877,753 B2 | 1/2024 | Connolly et al. |
| 11,878,131 B2 | 1/2024 | Pedersen et al. |
| 11,881,721 B2 | 1/2024 | Araujo et al. |
| 11,883,062 B2 | 1/2024 | Rawson |
| 11,883,274 B2 | 1/2024 | Schwammenthal et al. |
| D1,015,536 S | 2/2024 | Walsh |
| 11,890,085 B2 | 2/2024 | Duval et al. |
| 11,890,428 B2 | 2/2024 | Ito |
| 11,890,435 B2 | 2/2024 | Takagi |
| 11,896,474 B2 | 2/2024 | Hynes et al. |
| 11,896,482 B2 | 2/2024 | Delaloye et al. |
| 11,896,814 B2 | 2/2024 | Shambaugh, Jr. |

(56) References Cited

U.S. PATENT DOCUMENTS

| | | |
|---|---|---|
| 11,903,589 B2 | 2/2024 | Stahman et al. |
| 11,903,600 B2 | 2/2024 | Chu et al. |
| 11,903,831 B2 | 2/2024 | Shuey et al. |
| 11,903,857 B2 | 2/2024 | Folan |
| 11,911,072 B2 | 2/2024 | Fantuzzi et al. |
| 11,911,305 B2 | 2/2024 | Smith et al. |
| 11,918,186 B2 | 3/2024 | Chu et al. |
| 11,918,187 B2 | 3/2024 | Cahill et al. |
| 11,918,202 B2 | 3/2024 | Deuel et al. |
| 11,918,219 B2 | 3/2024 | Smith et al. |
| 11,918,470 B2 | 3/2024 | Jarral et al. |
| 11,918,752 B2 | 3/2024 | Tassoni et al. |
| 11,918,764 B2 | 3/2024 | Soltis et al. |
| 11,918,780 B2 | 3/2024 | Jagelski et al. |
| 11,925,315 B2 | 3/2024 | Chu et al. |
| 11,925,383 B2 | 3/2024 | Tada et al. |
| 11,925,386 B2 | 3/2024 | Favreau |
| 11,925,795 B2 | 3/2024 | Muller et al. |
| 11,930,996 B2 | 3/2024 | Dresher |
| 11,930,997 B2 | 3/2024 | Melito et al. |
| 11,931,003 B2 | 3/2024 | Congdon et al. |
| 11,931,058 B2 | 3/2024 | Spangler et al. |
| 11,931,068 B2 | 3/2024 | Fitterer et al. |
| 11,931,073 B2 | 3/2024 | Walsh et al. |
| 11,931,098 B2 | 3/2024 | Moriyama |
| 11,931,278 B2 | 3/2024 | Wood et al. |
| 11,931,528 B2 | 3/2024 | Rohl et al. |
| 11,931,530 B2 | 3/2024 | Campbell et al. |
| 11,937,774 B2 | 3/2024 | Wood et al. |
| 11,937,871 B2 | 3/2024 | Crawford et al. |
| 11,938,047 B2 | 3/2024 | Christakis et al. |
| 11,938,285 B2 | 3/2024 | Lau et al. |
| D1,028,246 S | 5/2024 | Delorenzo |
| 11,986,602 B2 | 5/2024 | Corbett |
| 11,986,604 B2 | 5/2024 | Siess |
| 11,996,699 B2 | 5/2024 | Vasconcelos Araujo et al. |
| 12,017,076 B2 | 6/2024 | Tan et al. |
| 12,023,476 B2 | 7/2024 | Tuval et al. |
| 12,023,477 B2 | 7/2024 | Siess |
| 12,059,559 B2 | 8/2024 | Muller et al. |
| 12,064,614 B2 | 8/2024 | Agah et al. |
| 12,076,497 B2 | 9/2024 | Fantuzzi et al. |
| 12,102,835 B2 | 10/2024 | Stotz et al. |
| 12,121,681 B2 | 10/2024 | Korkuch |
| 12,150,647 B2 | 11/2024 | Schuelke et al. |
| 12,161,855 B2 | 12/2024 | Hastie et al. |
| 12,161,857 B2 | 12/2024 | Saul et al. |
| 12,186,517 B2 | 1/2025 | Modlish et al. |
| 12,230,868 B2 | 2/2025 | Wenning et al. |
| 12,233,224 B2 | 2/2025 | Korkuch et al. |
| 12,233,250 B2 | 2/2025 | Stotz et al. |
| 12,239,799 B2 | 3/2025 | Corbett et al. |
| 12,263,330 B2 | 4/2025 | D'Ambrosio et al. |
| 12,268,860 B1 | 4/2025 | Fishman et al. |
| 12,290,673 B2 | 5/2025 | Jahangir |
| 2001/0016686 A1 | 8/2001 | Okada et al. |
| 2002/0052638 A1 | 5/2002 | Zadno-Azizi |
| 2002/0077600 A1 | 6/2002 | Sirimanne |
| 2002/0177324 A1 | 11/2002 | Metzler |
| 2003/0032941 A1 | 2/2003 | Boyle et al. |
| 2003/0040765 A1 | 2/2003 | Breznock |
| 2003/0125766 A1 | 7/2003 | Ding |
| 2003/0130581 A1 | 7/2003 | Salo et al. |
| 2004/0034411 A1* | 2/2004 | Quijano ............... A61F 2/2412 623/2.11 |
| 2004/0044266 A1 | 3/2004 | Siess et al. |
| 2004/0102674 A1 | 5/2004 | Zadini et al. |
| 2004/0124979 A1 | 7/2004 | Medema |
| 2004/0167410 A1 | 8/2004 | Hettrick |
| 2005/0006083 A1 | 1/2005 | Chen et al. |
| 2005/0107658 A1 | 5/2005 | Brockway |
| 2005/0107847 A1 | 5/2005 | Gruber et al. |
| 2005/0182435 A1 | 8/2005 | Andrews et al. |
| 2005/0272975 A1 | 12/2005 | McWeeney |
| 2006/0004423 A1 | 1/2006 | Boveja et al. |
| 2006/0155158 A1 | 7/2006 | Aboul-Hosn |
| 2006/0190036 A1 | 8/2006 | Wendel et al. |
| 2006/0196277 A1 | 9/2006 | Allen et al. |
| 2006/0217785 A1 | 9/2006 | Matei |
| 2006/0224110 A1 | 10/2006 | Scott et al. |
| 2007/0129767 A1 | 6/2007 | Wahlstrand |
| 2007/0282209 A1 | 12/2007 | Lui et al. |
| 2008/0015481 A1 | 1/2008 | Bergin et al. |
| 2008/0079392 A1 | 4/2008 | Baarman et al. |
| 2008/0082005 A1 | 4/2008 | Stern et al. |
| 2008/0086027 A1 | 4/2008 | Siess et al. |
| 2008/0097293 A1 | 4/2008 | Chin et al. |
| 2008/0097386 A1 | 4/2008 | Osypka |
| 2008/0114339 A1 | 5/2008 | McBride et al. |
| 2008/0183136 A1 | 7/2008 | Lenker et al. |
| 2008/0211455 A1 | 9/2008 | Park et al. |
| 2008/0238364 A1 | 10/2008 | Weber |
| 2008/0266922 A1 | 10/2008 | Mumtaz et al. |
| 2008/0269822 A1 | 10/2008 | Ljungstrom et al. |
| 2009/0010462 A1 | 1/2009 | Ekchian et al. |
| 2009/0024042 A1 | 1/2009 | Nunez et al. |
| 2009/0054840 A1 | 2/2009 | Drake et al. |
| 2009/0069886 A1 | 3/2009 | Suri et al. |
| 2009/0134711 A1 | 5/2009 | Issa et al. |
| 2009/0182200 A1 | 7/2009 | Golden |
| 2009/0198307 A1 | 8/2009 | Mi et al. |
| 2009/0198312 A1 | 8/2009 | Barker |
| 2009/0203957 A1 | 8/2009 | LaRose et al. |
| 2009/0276016 A1 | 11/2009 | Phillips et al. |
| 2009/0312650 A1 | 12/2009 | Maile et al. |
| 2010/0010582 A1 | 1/2010 | Carbunaru |
| 2010/0191035 A1 | 7/2010 | Kang et al. |
| 2010/0219967 A1 | 9/2010 | Kaufmann |
| 2010/0280568 A1 | 11/2010 | Bulkes et al. |
| 2010/0312310 A1 | 12/2010 | Meskens |
| 2010/0331918 A1 | 12/2010 | Digiore et al. |
| 2010/0331920 A1 | 12/2010 | Digiore et al. |
| 2011/0004278 A1 | 1/2011 | Aghassian |
| 2011/0034874 A1* | 2/2011 | Reitan ............... A61M 60/13 604/151 |
| 2011/0071336 A1 | 3/2011 | Yomtov |
| 2011/0124962 A1 | 5/2011 | Gordin |
| 2011/0137394 A1 | 6/2011 | Lunsford et al. |
| 2011/0196452 A1 | 8/2011 | Forsell |
| 2011/0224720 A1 | 9/2011 | Kassab et al. |
| 2011/0230821 A1 | 9/2011 | Babic |
| 2011/0282274 A1 | 11/2011 | Fulton, III |
| 2012/0019201 A1 | 1/2012 | Peterson |
| 2012/0022645 A1 | 1/2012 | Burke |
| 2012/0029265 A1 | 2/2012 | LaRose |
| 2012/0035645 A1 | 2/2012 | Gross |
| 2012/0050931 A1 | 3/2012 | Terry et al. |
| 2012/0068691 A1 | 3/2012 | Ejury |
| 2012/0112543 A1 | 5/2012 | van Wageningen et al. |
| 2012/0150291 A1 | 6/2012 | Aber |
| 2012/0158074 A1 | 6/2012 | Hall |
| 2012/0212178 A1 | 8/2012 | Kim |
| 2012/0235633 A1 | 9/2012 | Kesler et al. |
| 2012/0296313 A1 | 11/2012 | Andreacchi et al. |
| 2013/0069651 A1 | 3/2013 | Lumiani |
| 2013/0085318 A1 | 4/2013 | Toellner |
| 2013/0099585 A1 | 4/2013 | Von Novak et al. |
| 2013/0116575 A1 | 5/2013 | Mickle et al. |
| 2013/0178915 A1 | 7/2013 | Radziemski |
| 2013/0211324 A1 | 8/2013 | Voss et al. |
| 2013/0289334 A1 | 10/2013 | Badstibner |
| 2013/0303831 A1 | 11/2013 | Evans |
| 2013/0303970 A1 | 11/2013 | Keenan et al. |
| 2014/0005467 A1 | 1/2014 | Farnan et al. |
| 2014/0012282 A1 | 1/2014 | Fritsch |
| 2014/0028107 A1 | 1/2014 | Kwon |
| 2014/0039587 A1 | 2/2014 | Romero |
| 2014/0063666 A1 | 3/2014 | Kallal et al. |
| 2014/0094645 A1 | 4/2014 | Lafontaine et al. |
| 2014/0104898 A1 | 4/2014 | Yeo et al. |
| 2014/0107754 A1 | 4/2014 | Fuhs et al. |
| 2014/0135884 A1 | 5/2014 | Tockman et al. |
| 2014/0180250 A1 | 6/2014 | Belson |
| 2014/0194058 A1 | 7/2014 | Lee et al. |

(56) References Cited

U.S. PATENT DOCUMENTS

| | | |
|---|---|---|
| 2014/0233184 A1 | 8/2014 | Thompson et al. |
| 2014/0249603 A1 | 9/2014 | Yan et al. |
| 2014/0265620 A1 | 9/2014 | Hoarau et al. |
| 2014/0275727 A1 | 9/2014 | Bonde |
| 2014/0346884 A1 | 11/2014 | Fujita |
| 2015/0008755 A1 | 1/2015 | Sone |
| 2015/0028805 A1 | 1/2015 | Dearden et al. |
| 2015/0045696 A1 | 2/2015 | Osypka |
| 2015/0066082 A1 | 3/2015 | Moshe |
| 2015/0090372 A1 | 4/2015 | Branagan et al. |
| 2015/0119633 A1 | 4/2015 | Haselby et al. |
| 2015/0141738 A1 | 5/2015 | Toellner et al. |
| 2015/0151087 A1 | 6/2015 | Suzuki et al. |
| 2015/0196076 A1 | 7/2015 | Billingslea |
| 2015/0244166 A1 | 8/2015 | Chen |
| 2015/0290372 A1 | 10/2015 | Muller et al. |
| 2015/0290373 A1 | 10/2015 | Rudser et al. |
| 2015/0290432 A1 | 10/2015 | Mathews et al. |
| 2015/0306291 A1 | 10/2015 | Bonde et al. |
| 2015/0333532 A1 | 11/2015 | Han et al. |
| 2015/0343179 A1 | 12/2015 | Schumacher et al. |
| 2015/0359952 A1 | 12/2015 | Andrus et al. |
| 2015/0380972 A1 | 12/2015 | Fort |
| 2016/0022889 A1 | 1/2016 | Bluvshtein et al. |
| 2016/0067395 A1 | 3/2016 | Jimenez et al. |
| 2016/0081680 A1 | 3/2016 | Taylor |
| 2016/0087558 A1 | 3/2016 | Yamamoto |
| 2016/0095744 A1 | 4/2016 | Wolfertz et al. |
| 2016/0095968 A1 | 4/2016 | Rudser |
| 2016/0175501 A1 | 6/2016 | Schuermann |
| 2016/0226296 A1 | 8/2016 | Bae |
| 2016/0256620 A1 | 9/2016 | Scheckel et al. |
| 2016/0268846 A1 | 9/2016 | Akuzawa et al. |
| 2016/0271309 A1 | 9/2016 | Throckmorton et al. |
| 2016/0331980 A1 | 11/2016 | Strommer et al. |
| 2016/0336811 A1 | 11/2016 | Liu |
| 2016/0344302 A1 | 11/2016 | Inoue |
| 2017/0018967 A1 | 1/2017 | Berkhout |
| 2017/0043074 A1 | 2/2017 | Siess |
| 2017/0043170 A1 | 2/2017 | Guardiani |
| 2017/0047781 A1 | 2/2017 | Stanislawski et al. |
| 2017/0065267 A1 | 3/2017 | Fantuzzi et al. |
| 2017/0070082 A1 | 3/2017 | Zheng et al. |
| 2017/0080199 A1 | 3/2017 | Murphy |
| 2017/0136164 A1 | 5/2017 | Yeatts |
| 2017/0143938 A1 | 5/2017 | Ogle et al. |
| 2017/0143977 A1 | 5/2017 | Kaib et al. |
| 2017/0202575 A1 | 7/2017 | Stanfield et al. |
| 2017/0203104 A1 | 7/2017 | Nageri et al. |
| 2017/0209099 A1 | 7/2017 | Caron et al. |
| 2017/0215918 A1 | 8/2017 | Tao et al. |
| 2017/0231717 A1 | 8/2017 | Forsell |
| 2017/0232169 A1 | 8/2017 | Muller |
| 2017/0232170 A1 | 8/2017 | Jarvik |
| 2017/0232171 A1 | 8/2017 | Roehn et al. |
| 2017/0271919 A1 | 9/2017 | Von Novak, III et al. |
| 2017/0275799 A1 | 9/2017 | Chen |
| 2017/0288448 A1 | 10/2017 | Kranz et al. |
| 2017/0303375 A1 | 10/2017 | Woodhead |
| 2017/0312492 A1 | 11/2017 | Fantuzzi et al. |
| 2017/0353053 A1 | 12/2017 | Muratov |
| 2017/0354812 A1 | 12/2017 | Callaghan et al. |
| 2017/0361115 A1 | 12/2017 | Aghassian |
| 2017/0361117 A1 | 12/2017 | Aghassian |
| 2017/0368245 A1 | 12/2017 | Kantrowitz et al. |
| 2018/0001003 A1 | 1/2018 | Moran et al. |
| 2018/0015214 A1 | 1/2018 | Lynch |
| 2018/0078329 A1 | 3/2018 | Hansen et al. |
| 2018/0099076 A1 | 4/2018 | LaRose |
| 2018/0099078 A1 | 4/2018 | Tuseth et al. |
| 2018/0104397 A1 | 4/2018 | Schumacher |
| 2018/0126053 A1 | 5/2018 | Zilbershlag et al. |
| 2018/0194236 A1 | 7/2018 | Elshaer et al. |
| 2018/0200422 A1 | 7/2018 | Nguyen et al. |
| 2018/0207334 A1 | 7/2018 | Siess |
| 2018/0207336 A1 | 7/2018 | Solem |
| 2018/0243004 A1 | 8/2018 | von Segesser et al. |
| 2018/0256796 A1 | 9/2018 | Hansen |
| 2018/0256800 A1 | 9/2018 | Conyers et al. |
| 2018/0269724 A1 | 9/2018 | Smith |
| 2018/0269930 A1 | 9/2018 | Kwon |
| 2018/0278099 A1 | 9/2018 | Hong |
| 2018/0280708 A1 | 10/2018 | Escalona et al. |
| 2018/0287405 A1 | 10/2018 | Govindaraj |
| 2018/0296742 A1 | 10/2018 | Toellner |
| 2018/0303990 A1 | 10/2018 | Siess et al. |
| 2018/0316209 A1 | 11/2018 | Gliner |
| 2018/0318547 A1 | 11/2018 | Yokoyama |
| 2018/0326131 A1 | 11/2018 | Muller et al. |
| 2019/0001103 A1 | 1/2019 | Korkuch |
| 2019/0004037 A1 | 1/2019 | Zhang et al. |
| 2019/0015232 A1 | 1/2019 | Tuseth et al. |
| 2019/0015568 A1 | 1/2019 | Tuseth |
| 2019/0015570 A1 | 1/2019 | Muller |
| 2019/0060543 A1 | 2/2019 | Khanal et al. |
| 2019/0068004 A1 | 2/2019 | Louis |
| 2019/0069898 A1 | 3/2019 | Farnan |
| 2019/0074726 A1 | 3/2019 | Hosotani |
| 2019/0076167 A1 | 3/2019 | Fantuzzi et al. |
| 2019/0083082 A1 | 3/2019 | Tassoni, Jr. et al. |
| 2019/0083690 A1 | 3/2019 | Siess et al. |
| 2019/0097447 A1 | 3/2019 | Partovi |
| 2019/0120905 A1 | 4/2019 | Wong |
| 2019/0167122 A1 | 6/2019 | Obermiller et al. |
| 2019/0167305 A1 | 6/2019 | Pedersen et al. |
| 2019/0175808 A1 | 6/2019 | Zilbershlag et al. |
| 2019/0184078 A1 | 6/2019 | Zilbershlag et al. |
| 2019/0222064 A1 | 7/2019 | Du et al. |
| 2019/0223877 A1 | 7/2019 | Nitzen et al. |
| 2019/0224390 A1 | 7/2019 | Barry |
| 2019/0231523 A1* | 8/2019 | Lombardi ............ A61F 2/2436 |
| 2019/0232025 A1 | 8/2019 | Tao et al. |
| 2019/0247627 A1 | 8/2019 | Korkuch et al. |
| 2019/0267913 A1 | 8/2019 | Lim |
| 2019/0282741 A1 | 9/2019 | Franano et al. |
| 2019/0290817 A1 | 9/2019 | Guo et al. |
| 2019/0298974 A1 | 10/2019 | Siess et al. |
| 2019/0305613 A1 | 10/2019 | Oshima |
| 2019/0321527 A1 | 10/2019 | King et al. |
| 2019/0344000 A1 | 11/2019 | Kushwaha et al. |
| 2019/0344052 A1 | 11/2019 | Klepetko |
| 2019/0351120 A1 | 11/2019 | Kushwaha et al. |
| 2019/0365975 A1 | 12/2019 | Muller et al. |
| 2019/0381226 A1 | 12/2019 | Morozov et al. |
| 2019/0393735 A1 | 12/2019 | Lee et al. |
| 2020/0000988 A1 | 1/2020 | Epple |
| 2020/0000989 A1 | 1/2020 | Matheis et al. |
| 2020/0022811 A1* | 1/2020 | Griswold ............ A61F 2/2439 |
| 2020/0023109 A1* | 1/2020 | Epple ................. A61M 60/886 |
| 2020/0023110 A1 | 1/2020 | Jahangir |
| 2020/0023113 A1 | 1/2020 | Epple et al. |
| 2020/0028376 A1 | 1/2020 | Ha |
| 2020/0054806 A1 | 2/2020 | Sun |
| 2020/0054857 A1 | 2/2020 | Scheckel |
| 2020/0054861 A1 | 2/2020 | Korkuch et al. |
| 2020/0086021 A1 | 3/2020 | Jeevanandam et al. |
| 2020/0094019 A1 | 3/2020 | Siess et al. |
| 2020/0121905 A1 | 4/2020 | Zoll |
| 2020/0129684 A1 | 4/2020 | Pfeffer et al. |
| 2020/0136421 A1 | 4/2020 | Kim |
| 2020/0139028 A1 | 5/2020 | Scheckel et al. |
| 2020/0139032 A1 | 5/2020 | Bryson et al. |
| 2020/0147283 A1 | 5/2020 | Tanner et al. |
| 2020/0155739 A1 | 5/2020 | Siess et al. |
| 2020/0164125 A1 | 5/2020 | Muller et al. |
| 2020/0179657 A1 | 6/2020 | Liu |
| 2020/0227954 A1 | 7/2020 | Ding et al. |
| 2020/0261633 A1 | 8/2020 | Spanier |
| 2020/0345337 A1 | 11/2020 | Muller et al. |
| 2020/0350812 A1 | 11/2020 | Vogt et al. |
| 2020/0366121 A1 | 11/2020 | Guedon |
| 2020/0373768 A1 | 11/2020 | Danilovic |
| 2021/0052793 A1 | 2/2021 | Struthers et al. |
| 2021/0057804 A1 | 2/2021 | Wenning |

(56) References Cited

U.S. PATENT DOCUMENTS

| | | | |
|---|---|---|---|
| 2021/0093836 A1 | 4/2021 | Fantuzzi | |
| 2021/0143688 A1 | 5/2021 | Agrawal et al. | |
| 2021/0146116 A1 | 5/2021 | Siess | |
| 2021/0205585 A1 | 7/2021 | Ullmann | |
| 2021/0275791 A1 | 9/2021 | Korkuch et al. | |
| 2021/0290939 A1* | 9/2021 | Baumbach | A61M 60/178 |
| 2021/0322011 A1 | 10/2021 | Schuelke et al. | |
| 2021/0336484 A1 | 10/2021 | Araujo et al. | |
| 2021/0339009 A1 | 11/2021 | Stotz et al. | |
| 2021/0351628 A1 | 11/2021 | Araujo et al. | |
| 2021/0379352 A1 | 12/2021 | Schlebusch et al. | |
| 2021/0379360 A1 | 12/2021 | Schellenberg | |
| 2021/0386990 A1 | 12/2021 | Stotz et al. | |
| 2021/0393944 A1 | 12/2021 | Wenning | |
| 2021/0399582 A1 | 12/2021 | Araujo et al. | |
| 2022/0008053 A1 | 1/2022 | Fitzgerald et al. | |
| 2022/0032036 A1 | 2/2022 | Baumbach et al. | |
| 2022/0080184 A1 | 3/2022 | Clifton et al. | |
| 2022/0080185 A1 | 3/2022 | Clifton et al. | |
| 2022/0096125 A1 | 3/2022 | Fantuzzi et al. | |
| 2022/0103023 A1 | 3/2022 | Govindaraj | |
| 2022/0139614 A1 | 5/2022 | Diekhans et al. | |
| 2022/0161018 A1 | 5/2022 | Mitze et al. | |
| 2022/0161019 A1 | 5/2022 | Mitze et al. | |
| 2022/0161021 A1 | 5/2022 | Mitze et al. | |
| 2022/0166253 A1 | 5/2022 | Forsell | |
| 2022/0320901 A1 | 10/2022 | Araujo et al. | |
| 2022/0339400 A1 | 10/2022 | Fantuzzi et al. | |
| 2022/0407403 A1 | 12/2022 | Vogt et al. | |
| 2022/0417673 A1 | 12/2022 | Narampanawe | |
| 2023/0091199 A1 | 3/2023 | Siess et al. | |
| 2023/0145482 A1* | 5/2023 | Garrigue | A61M 60/178 600/16 |
| 2023/0173250 A1 | 6/2023 | Stigloher | |
| 2023/0191141 A1 | 6/2023 | Wenning et al. | |
| 2023/0258694 A1 | 8/2023 | Vijayakumar | |
| 2023/0277833 A1 | 9/2023 | Sharma et al. | |
| 2023/0293878 A1 | 9/2023 | Christof et al. | |
| 2023/0352236 A1 | 11/2023 | Diekhans et al. | |
| 2023/0381526 A1 | 11/2023 | Stotz et al. | |
| 2023/0398330 A1 | 12/2023 | Mitze et al. | |
| 2024/0074828 A1 | 3/2024 | Wenning | |
| 2024/0165392 A1 | 5/2024 | Liu et al. | |
| 2024/0186828 A1 | 6/2024 | Chu | |
| 2024/0269451 A1 | 8/2024 | Siess et al. | |
| 2024/0269459 A1 | 8/2024 | Schellenberg et al. | |
| 2025/0082922 A1 | 3/2025 | Fabiunke et al. | |
| 2025/0134652 A1* | 5/2025 | Maiorano | A61F 2/2418 |

FOREIGN PATENT DOCUMENTS

| | | | |
|---|---|---|---|
| CN | 1524000 | 8/2004 | |
| CN | 102438552 | 5/2012 | |
| CN | 103143072 | 6/2013 | |
| CN | 103942511 | 7/2014 | |
| CN | 104274873 | 1/2015 | |
| CN | 204106671 | 1/2015 | |
| CN | 104888293 | 3/2017 | |
| CN | 106512117 | 3/2017 | |
| CN | 106776441 | 5/2017 | |
| CN | 107080871 | 8/2017 | |
| CN | 206443963 | 8/2017 | |
| CN | 107206139 | 9/2017 | |
| CN | 107412892 | 12/2017 | |
| CN | 207708250 | 8/2018 | |
| CN | 106902404 | 8/2019 | |
| CN | 110237327 | 9/2019 | |
| CN | 209790495 | 12/2019 | |
| CN | 110665079 | 1/2020 | |
| CN | 112168427 A * | 1/2021 | A61F 2/2454 |
| CN | 113413544 | 9/2021 | |
| CN | 215691046 | 2/2022 | |
| CN | 114886614 A * | 8/2022 | A61F 2/243 |
| CN | 115916111 A * | 4/2023 | A61F 2/0108 |
| CN | 218922664 | 4/2023 | |
| CN | 116271502 A * | 6/2023 | A61M 60/13 |
| CN | 116688321 | 10/2023 | |
| CN | 117959584 A * | 5/2024 | |
| CN | 118717356 A * | 10/2024 | A61F 2/2466 |
| CN | 119033506 A * | 11/2024 | A61F 2/2466 |
| DE | 103 02 550 | 8/2004 | |
| DE | 10 2009 011 726 | 9/2010 | |
| DE | 10 2009 047 845 | 3/2011 | |
| DE | 11 2009 000 185 | 3/2013 | |
| DE | 10 2012 200 912 | 7/2013 | |
| DE | 11 2012 005 944 | 12/2014 | |
| DE | 202013007408 U1 * | 12/2014 | A61M 1/1008 |
| DE | 10 2014 212 323 | 12/2015 | |
| DE | 10 2016 106 683 | 10/2016 | |
| DE | 10 2016 225 862 | 6/2017 | |
| DE | 10 2016 203 172 | 8/2017 | |
| DE | 10 2016 122 268 | 5/2018 | |
| DE | 10 2017 213 475 | 2/2019 | |
| DE | 10 2018 204 604 | 10/2019 | |
| DE | 10 2018 204 610 | 10/2019 | |
| DE | 10 2018 206 714 | 11/2019 | |
| DE | 10 2018 206 724 | 11/2019 | |
| DE | 10 2018 206 725 | 11/2019 | |
| DE | 10 2018 206 727 | 11/2019 | |
| DE | 10 2018 206 731 | 11/2019 | |
| DE | 10 2018 206 750 | 11/2019 | |
| DE | 10 2018 206 754 | 11/2019 | |
| DE | 10 2018 206 758 | 11/2019 | |
| DE | 10 2018 208 537 | 12/2019 | |
| DE | 10 2018 208 564 | 12/2019 | |
| DE | 10 2018 211 297 | 1/2020 | |
| DE | 10 2018 222 505 | 6/2020 | |
| EP | 0 064 212 | 11/1982 | |
| EP | 0 411 605 | 2/1991 | |
| EP | 0 629 412 | 12/1994 | |
| EP | 0 930 086 | 7/1999 | |
| EP | 0 898 481 | 1/2002 | |
| EP | 1 105 181 | 2/2004 | |
| EP | 1 660 164 | 4/2009 | |
| EP | 2 039 390 | 11/2010 | |
| EP | 2 436 417 | 4/2012 | |
| EP | 2 716 242 | 4/2014 | |
| EP | 2 752 209 | 7/2014 | |
| EP | 2 782 210 | 9/2014 | |
| EP | 2 859 911 | 4/2015 | |
| EP | 2 015 821 | 5/2015 | |
| EP | 2 519 273 | 8/2015 | |
| EP | 2 680 896 | 1/2016 | |
| EP | 2 966 753 | 1/2016 | |
| EP | 2 475 415 | 6/2016 | |
| EP | 2 454 799 | 9/2016 | |
| EP | 2 934 649 | 11/2016 | |
| EP | 2 646 068 | 3/2017 | |
| EP | 2 709 689 | 4/2017 | |
| EP | 3 220 505 | 9/2017 | |
| EP | 3 378 421 | 9/2018 | |
| EP | 3 398 625 | 11/2018 | |
| EP | 3 131 599 | 2/2019 | |
| EP | 3 508 245 | 7/2019 | |
| EP | 3 187 222 | 9/2019 | |
| EP | 3 536 360 | 9/2019 | |
| EP | 3 077 038 | 10/2019 | |
| EP | 2 962 720 | 1/2020 | |
| EP | 1 819 391 | 2/2020 | |
| EP | 3 189 862 | 2/2020 | |
| EP | 3 618 886 | 3/2020 | |
| EP | 2 922 593 | 4/2020 | |
| EP | 3 180 064 | 4/2020 | |
| EP | 3 131 597 | 12/2020 | |
| EP | 3 357 523 | 1/2021 | |
| EP | 3 423 126 | 2/2021 | |
| EP | 3 490 628 | 2/2021 | |
| EP | 3 198 677 | 3/2021 | |
| EP | 3 248 647 | 3/2021 | |
| EP | 3 419 711 | 3/2021 | |
| EP | 3 436 106 | 3/2021 | |
| EP | 3 509 661 | 3/2021 | |
| EP | 3 528 863 | 3/2021 | |

(56) References Cited

FOREIGN PATENT DOCUMENTS

| | | |
|---|---|---|
| EP | 4 271 461 | 3/2021 |
| EP | 3 436 105 | 4/2021 |
| EP | 3 116 407 | 5/2021 |
| EP | 3 131 600 | 6/2021 |
| EP | 3 131 615 | 6/2021 |
| EP | 3 827 876 | 6/2021 |
| EP | 2 608 731 | 7/2021 |
| EP | 3 323 465 | 7/2021 |
| EP | 3 570 926 | 7/2021 |
| EP | 3 851 151 | 7/2021 |
| EP | 3 247 440 | 8/2021 |
| EP | 3 656 293 | 8/2021 |
| EP | 3 006 072 | 9/2021 |
| EP | 2 599 510 | 10/2021 |
| EP | 3 077 018 | 10/2021 |
| EP | 3 351 209 | 10/2021 |
| EP | 3 485 936 | 10/2021 |
| EP | 3 592 411 | 11/2021 |
| EP | 3 618 884 | 11/2021 |
| EP | 3 914 330 | 12/2021 |
| EP | 3 539 613 | 2/2022 |
| EP | 2 858 718 | 3/2022 |
| EP | 3 337 530 | 3/2022 |
| EP | 3 624 867 | 3/2022 |
| EP | 2 967 630 | 4/2022 |
| EP | 3 755 237 | 4/2022 |
| EP | 3 978 060 | 4/2022 |
| EP | 3 153 205 | 5/2022 |
| EP | 3 407 811 | 5/2022 |
| EP | 3 124 071 | 6/2022 |
| EP | 3 636 312 | 6/2022 |
| EP | 3 661 436 | 6/2022 |
| EP | 3 497 775 | 7/2022 |
| EP | 3 231 395 | 8/2022 |
| EP | 3 711 788 | 8/2022 |
| EP | 4 039 320 | 8/2022 |
| EP | 2 654 883 | 9/2022 |
| EP | 3 485 819 | 9/2022 |
| EP | 3 487 550 | 9/2022 |
| EP | 3 756 721 | 9/2022 |
| EP | 3 834 876 | 9/2022 |
| EP | 3 600 477 | 10/2022 |
| EP | 3 849 646 | 10/2022 |
| EP | 3 000 493 | 11/2022 |
| EP | 3 028 736 | 11/2022 |
| EP | 3 077 035 | 11/2022 |
| EP | 3 305 357 | 11/2022 |
| EP | 3 389 530 | 11/2022 |
| EP | 3 570 762 | 11/2022 |
| EP | 3 579 905 | 11/2022 |
| EP | 3 808 408 | 11/2022 |
| EP | 3 858 422 | 11/2022 |
| EP | 3 866 876 | 11/2022 |
| EP | 3 199 198 | 12/2022 |
| EP | 3 270 999 | 12/2022 |
| EP | 3 398 562 | 12/2022 |
| EP | 3 402 562 | 12/2022 |
| EP | 2 892 583 | 1/2023 |
| EP | 3 597 231 | 1/2023 |
| EP | 3 856 275 | 1/2023 |
| EP | 3 003 420 | 2/2023 |
| EP | 3 538 173 | 3/2023 |
| EP | 3 946 511 | 4/2023 |
| EP | 3 826 104 | 5/2023 |
| EP | 3 551 271 | 7/2023 |
| EP | 3 692 933 | 9/2023 |
| EP | 3 713 634 | 9/2023 |
| EP | 3 773 130 | 9/2023 |
| EP | 3 895 638 | 9/2023 |
| EP | 3 903 701 | 9/2023 |
| EP | 3 178 515 | 10/2023 |
| EP | 3 253 302 | 10/2023 |
| EP | 3 603 727 | 10/2023 |
| EP | 3 773 129 | 10/2023 |
| EP | 3 777 952 | 10/2023 |
| EP | 4 052 754 | 10/2023 |
| EP | 4 149 606 | 10/2023 |
| EP | 3 515 525 | 11/2023 |
| EP | 3 583 927 | 11/2023 |
| EP | 3 744 362 | 11/2023 |
| EP | 3 766 428 | 11/2023 |
| EP | 3 773 363 | 11/2023 |
| EP | 3 840 670 | 11/2023 |
| EP | 3 711 698 | 12/2023 |
| EP | 3 752 236 | 12/2023 |
| EP | 3 349 671 | 1/2024 |
| EP | 3 349 839 | 1/2024 |
| EP | 3 443 915 | 1/2024 |
| EP | 3 487 421 | 1/2024 |
| EP | 3 784 305 | 1/2024 |
| EP | 3 925 659 | 1/2024 |
| EP | 3 242 613 | 2/2024 |
| EP | 3 509 504 | 2/2024 |
| EP | 3 518 836 | 2/2024 |
| EP | 3 534 805 | 2/2024 |
| EP | 3 566 636 | 2/2024 |
| EP | 3 603 728 | 2/2024 |
| EP | 3 700 464 | 2/2024 |
| EP | 3 718 588 | 2/2024 |
| EP | 3 768 342 | 2/2024 |
| EP | 3 820 412 | 2/2024 |
| EP | 3 053 532 | 3/2024 |
| EP | 3 142 573 | 3/2024 |
| EP | 3 275 499 | 3/2024 |
| EP | 3 397 147 | 3/2024 |
| EP | 3 424 551 | 3/2024 |
| EP | 3 492 042 | 3/2024 |
| EP | 3 528 885 | 3/2024 |
| EP | 3 563 805 | 3/2024 |
| EP | 3 927 254 | 3/2024 |
| EP | 3 955 796 | 3/2024 |
| EP | 4 037 574 | 3/2024 |
| EP | 4 140 532 | 5/2024 |
| EP | 3 970 765 | 7/2024 |
| EP | 3 789 054 | 8/2024 |
| EP | 3 793 633 | 8/2024 |
| EP | 4 429 750 | 9/2024 |
| EP | 3 534 985 | 10/2024 |
| EP | 3 893 957 | 10/2024 |
| EP | 3 641 845 | 11/2024 |
| EP | 3 643 350 | 11/2024 |
| EP | 4 034 221 | 11/2024 |
| EP | 3 522 947 | 2/2025 |
| EP | 4 429 754 | 2/2025 |
| EP | 4 429 751 | 3/2025 |
| EP | 4 429 752 | 3/2025 |
| EP | 4 429 753 | 3/2025 |
| EP | 3 958 921 | 5/2025 |
| GB | 2 451 161 | 12/2011 |
| GB | 2 545 750 | 6/2017 |
| JP | S59-076463 | 5/1984 |
| JP | H04-176471 | 6/1992 |
| JP | H09-028664 | 2/1997 |
| JP | H11-178249 | 7/1999 |
| JP | 4706886 | 6/2011 |
| JP | 2013-013216 | 1/2013 |
| JP | 6267625 | 1/2018 |
| JP | 2018-046708 | 3/2018 |
| KR | 10-1185112 | 9/2012 |
| WO | WO 89/006513 | 1/1989 |
| WO | WO 97/037697 | 10/1997 |
| WO | WO 2005/007024 | 1/2005 |
| WO | WO 2005/028014 | 3/2005 |
| WO | WO 2007/006055 | 1/2007 |
| WO | WO 2007/044510 | 4/2007 |
| WO | WO 2008/106103 | 9/2008 |
| WO | WO-2008106103 A2 * 9/2008 ............ A61M 1/101 |  |
| WO | WO 2009/023905 | 2/2009 |
| WO | WO 2009/029977 | 3/2009 |
| WO | WO 2009/114456 | 9/2009 |
| WO | WO 2010/014418 | 2/2010 |
| WO | WO 2010/042054 | 4/2010 |
| WO | WO 2010/092347 | 8/2010 |
| WO | WO 2011/007300 | 1/2011 |

(56) References Cited

FOREIGN PATENT DOCUMENTS

| | | |
|---|---|---|
| WO | WO 2011/096975 | 8/2011 |
| WO | WO 2011/160858 | 12/2011 |
| WO | WO 2012/147061 | 11/2012 |
| WO | WO 2013/013248 | 1/2013 |
| WO | WO 2013/092971 | 6/2013 |
| WO | WO 2013/093058 | 6/2013 |
| WO | WO 2013/164831 | 11/2013 |
| WO | WO 2014/096408 | 6/2014 |
| WO | WO 2015/019132 | 2/2015 |
| WO | WO 2015/152732 | 10/2015 |
| WO | WO 2016/028644 | 2/2016 |
| WO | WO 2016/055368 | 4/2016 |
| WO | WO 2017/021846 | 2/2017 |
| WO | WO 2017/053988 | 3/2017 |
| WO | WO 2017/060257 | 4/2017 |
| WO | WO 2017/066257 | 4/2017 |
| WO | WO 2017/089440 | 6/2017 |
| WO | WO 2017/118738 | 7/2017 |
| WO | WO-2017118738 A1 * 7/2017 ............ A61B 17/11 |  |
| WO | WO 2017/147103 | 8/2017 |
| WO | WO 2017/157884 | 9/2017 |
| WO | WO 2017/165372 | 9/2017 |
| WO | WO 2017/194562 | 11/2017 |
| WO | WO 2017/213032 | 12/2017 |
| WO | WO 2017/218349 | 12/2017 |
| WO | WO 2018/033799 | 2/2018 |
| WO | WO 2018/081040 | 5/2018 |
| WO | WO-2018078615 A1 * 5/2018 ............ A61M 60/13 |  |
| WO | WO 2018/100192 | 6/2018 |
| WO | WO 2018/165519 | 9/2018 |
| WO | WO 2018/202779 | 11/2018 |
| WO | WO 2018/234454 | 12/2018 |
| WO | WO 2019/025258 | 2/2019 |
| WO | WO 2019/025259 | 2/2019 |
| WO | WO 2019/025260 | 2/2019 |
| WO | WO 2019/035804 | 2/2019 |
| WO | WO 2019/038343 | 2/2019 |
| WO | WO 2019/038345 | 2/2019 |
| WO | WO 2019/055591 | 3/2019 |
| WO | WO 2019/067233 | 4/2019 |
| WO | WO 2019/101786 | 5/2019 |
| WO | WO-2019118371 A1 * 6/2019 ........... A61F 2/2463 |  |
| WO | WO 2019/145253 | 8/2019 |
| WO | WO 2019/158996 | 8/2019 |
| WO | WO 2019/161245 | 8/2019 |
| WO | WO 2019/180181 | 9/2019 |
| WO | WO 2019/183247 | 9/2019 |
| WO | WO 2019/185511 | 10/2019 |
| WO | WO 2019/185512 | 10/2019 |
| WO | WO 2019/191245 | 10/2019 |
| WO | WO 2019/193604 | 10/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/219883 | 11/2019 |
| WO | WO 2019/229206 | 12/2019 |
| WO | WO 2019/229207 | 12/2019 |
| WO | WO 2019/229224 | 12/2019 |
| WO | WO 2019/234151 | 12/2019 |
| WO | WO 2019/241556 | 12/2019 |
| WO | WO 2019/244031 | 12/2019 |
| WO | WO 2020/003110 | 1/2020 |
| WO | WO 2020/011760 | 1/2020 |
| WO | WO 2020/089429 | 5/2020 |
| WO | WO 2020/123333 | 6/2020 |
| WO | WO 2020/132211 | 6/2020 |
| WO | WO 2020/137708 | 7/2020 |
| WO | WO 2020/219430 | 10/2020 |
| WO | WO 2021/062265 | 4/2021 |
| WO | WO 2021/150777 | 7/2021 |
| WO | WO 2022/011095 | 1/2022 |
| WO | WO 2022/032286 | 2/2022 |
| WO | WO 2022/091784 | 5/2022 |
| WO | WO 2022/109589 | 5/2022 |
| WO | WO 2022/109591 | 5/2022 |
| WO | WO 2023/003937 | 1/2023 |
| WO | WO-2023040546 A1 * 3/2023 ............ A61M 60/13 |  |
| WO | WO 2023/076869 | 5/2023 |
| WO | WO 2024/125157 | 5/2023 |
| WO | WO-2023112044 A1 * 6/2023 ........... A61F 2/2442 |  |
| WO | WO 2023/230157 | 11/2023 |
| WO | WO 2024/243154 | 11/2024 |
| WO | WO 2025/075927 | 4/2025 |

OTHER PUBLICATIONS

International Search Report and Written Opinion received in PCT Application No. PCT/EP2019/064158, dated Sep. 9, 2019 in 12 pages.
Atkinson et al., "Pulse-Doppler Ultrasound and Its Clinical Application", The Yale Journal of Biology and Medicine, 1977, vol. 50, pp. 367-373.
Chung et al., "Improved Efficiency Characteristics of Wireless Power Charging System for Superconducting MAGLEV Train Using Inserted Permanent Magnets," 2018 IEEE International Symposium on Electromagnetic Compatibility, 2018, pp. 564-567.
"ECG Electrodes product comparison chart," 3M.com, 2018, https://multimedia.3m.com/mws/media/1490883O/red-dot-ecg-electrodes-comparison-chart.pdf, accessed May 18, 2025, 1 page.
"Edwards Sapien 3 Kit—Transapical and Transaortic", Edwards Lifesciences, Released Nov. 8, 2016, pp. 11. chrome-extension://efaidnbmnnnibpcajpcglclefindmkaj/https://edwardsprod.blob.core.windows.net/media/De/sapien3/doc-0045537b%20-%20certitude.pdf.
Gopinath, Divya, "A System for Impedance Characterization of Coronary Stents", University of Strathclyde Engineering, Thesis, Aug. 2015, pp. 77.
HeartMate 3™ Left Ventricular Assist System, Instructions for Use, Thoratec Corporation, Aug. 2017, pp. 536. [Uploaded in 3 parts].
Leguy et al., "Assessment of Blood Volume Flow in Slightly Curved Arteries from a Single Velocity Profile", Journal of Biomechanics, 2009, pp. 1664-1672.
Mack-Haynes, Robin, "Fasteners Made Easy," New Mexico State University, https://pubs.nmsu.edu/_c/C232.pdf, accessed May 18, 2025, pp. 8.
Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.
Park et al., "A Novel Electrical Potential Sensing Method for in Vitro Stent Fracture Monitoring and Detection", Jan. 1, 2011, vol. 21, No. 4, pp. 213-222.
Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.
"Transvalvular Insertion Tool (TVI)", Pressure Products, Feb. 2013, https://www.pressure-products.com/wip/tvi.html, as printed Jul. 25, 2024 in 2 pages.
Vieli, A., "Doppler Flow Determination", BJA: British Journal of Anaesthesia, 1988, vol. 60, pp. 107S-112S.

* cited by examiner

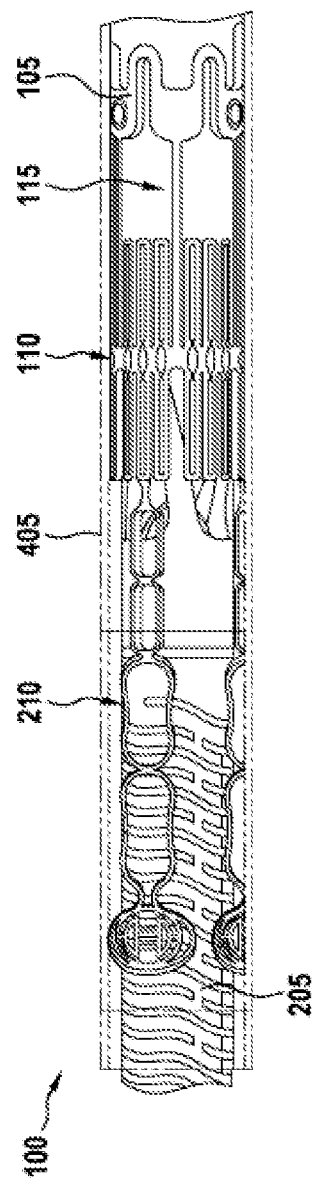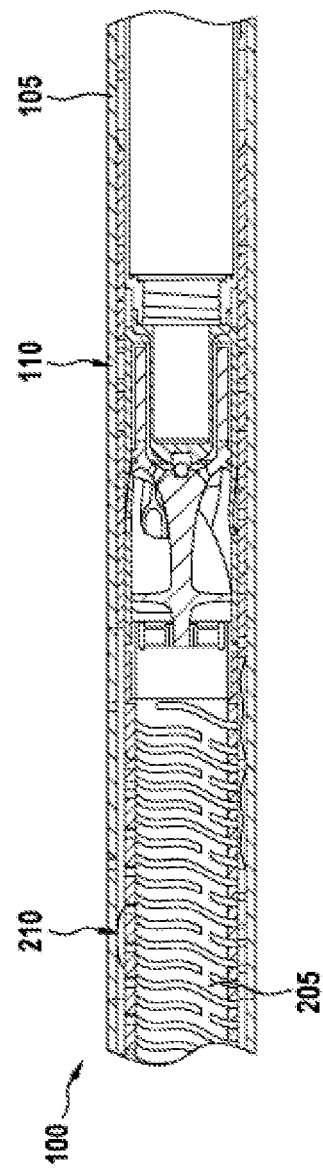
Fig. 4
Fig. 5

APPARATUS FOR ANCHORING A VENTRICULAR ASSIST SYSTEM IN A BLOOD VESSEL, OPERATING METHOD, PRODUCTION METHOD FOR PRODUCING AN APPARATUS AND VENTRICULAR ASSIST SYSTEM

BACKGROUND

Field

The invention relates to an apparatus for anchoring a cardiac support system in a blood vessel, a method for operating such an apparatus and a production method for producing such an apparatus and a cardiac support system.

Description of the Related Art

Cardiac support systems for long-term therapy are typically implanted via a complete or partial opening of the sternum, whereby a heart-lung machine can be used to enable extracorporeal blood circulation. This often involves punching a hole in the structural integrity of the myocardial tissue and the body's main artery, the aorta. Short-term intravascular cardiac support systems are delivered either percutaneously, i.e. through the skin, or surgically via various arterial accesses, for example via the femoral artery. The final positioning of the cardiac support systems can be visually supported intraoperatively, for example by means of ultrasound or radiological fluoroscopy. The implanted cardiac support systems have a high risk of dislocation, however, because there is no local fixing of the cardiac support system. The cardiac support system can therefore shift after implantation because it is not anchored at the implantation site, which can lead to malfunctioning of the pump or to an interruption of the therapy with the cardiac support system.

SUMMARY

The object of the invention is to create an apparatus that makes it possible to place a medical system, e.g. a cardiac support system, but also an implant, in particular in a blood vessel, e.g. inside the aorta, such that it has a generally constant spatial position relative to a section of the human or animal body, even over long periods of time, i.e. hours, days, weeks, months or, if necessary, even years.

This object is achieved by the apparatus for anchoring a cardiac support system in a blood vessel and the production method for an apparatus for anchoring a cardiac support system in a blood vessel, as described and claimed herein. Advantageous embodiments of the invention are specified in the dependent claims.

The apparatus for anchoring a cardiac support system in a blood vessel and a method for operating an apparatus for anchoring a cardiac support system as well as the production method for producing a corresponding apparatus and a cardiac support system having a corresponding apparatus according to the main claims are presented in the following. Advantageous further developments and improvements of the apparatus specified in the independent claim are possible using the measures listed in the dependent claims.

With the approach presented here, an implant, for example a cardiac support system, can be positioned and anchored in the blood vessel, in particular inside the aorta, by means of an apparatus with or without a spatial relationship to the aortic valve. For this purpose, the apparatus can be fixed to a heart pump. To be able to insert the cardiac support system in a minimally invasive manner, the apparatus can advantageously be folded, and the apparatus is designed such that it can unfold at the destination to position and anchor the cardiac support system. Using the apparatus, the cardiac support system can be aligned at the destination and placed in a targeted manner. The position of the cardiac support system advantageously remains unchanged in the long term due to the anchoring provided by the apparatus, as a result of which shifting or dislocation of the cardiac support system can be eliminated.

An apparatus for anchoring a cardiac support system in a blood vessel will be presented. The apparatus can assume an insertion state for inserting the cardiac support system into the blood vessel. The apparatus can also assume an anchoring state for anchoring the cardiac support system in the blood vessel. The apparatus comprises at least one fixing means for fixing the apparatus to the cardiac support system, a crown and a connection means, which is configured to connect the crown to the fixing means. The crown consists of at least one unfolding element. The unfolding element is designed to unfold during a transition from the insertion state into the anchoring state in order to increase the diameter of the crown to anchor the apparatus in the blood vessel.

The apparatus can be made of a biocompatible material to allow the apparatus to grow together with the blood vessel, for example the aorta, during long-term use of the apparatus. The apparatus can also be made of an elastic material that simultaneously exhibits a certain degree of rigidity, for example Nitinol. The cardiac support system can be a heart pump, for example, such as a right ventricular support system, a left ventricular support system, a biventricular support system or a vascular or valve prosthesis. The apparatus can furthermore also be used to position another component in a blood vessel and anchor it at its destination, for example a vascular or intracavitary implant such as a gastrointestinal, intrathecal, or intravesical implant. The insertion state can, for example, be understood to be the state assumed by the apparatus for insertion or during insertion of the cardiac support system into the blood vessel. The apparatus can be fixed to the heart pump, for example, and folded such that the apparatus can be inserted into a catheter along with the cardiac support system for minimally invasive insertion. The apparatus and the cardiac support system can be inserted in a minimally invasive manner through the leg artery, the femoral artery, for example. In the insertion state, the apparatus can correspondingly have a diameter that is less than the diameter of a human aorta. The anchoring state can be understood to be a state in which, after being inserted and aligned at the destination, the apparatus is unfolded to increase the diameter of the crown in order to anchor the cardiac support system in a force-locking manner at the destination and thus advantageously prevent shifting or dislocation of the cardiac support system. In the anchoring state, i.e. in the unfolded state, the apparatus or a component of the apparatus, for example the crown, can have an inner diameter that is slightly larger than the inner diameter of the blood vessel in which it is anchored, for example a total inner diameter in the range of 20-30 mm, for example 23 mm, for anchoring to or behind a human aortic valve. In the anchoring state, the outer contour of at least one part of the apparatus, for example the crown, can furthermore have a shape that corresponds to the not exactly circular aortic anatomy of a human aorta. The apparatus can thus be held at the destination in the anchoring state via a radial frictional connection.

The fixing means can be configured to fix the apparatus to an implant, for example the cardiac support system. For this purpose, the fixing means can comprise at least one fixing element for creating a form-locking and/or force-locking connection to a counterfixing element disposed on the implant. The crown can be shaped like a ring. Depending on the embodiment, one single unfolding element can be shaped like a ring, or a plurality of unfolding elements can be strung together in a ring-like manner. Unfolding allows the at least one unfolding element to expand. The connection means can comprise at least one elongated, for example wire-shaped, strut, which is fastened to both the crown and the fixing means. The connection means can be designed to be flexible in order to allow the diameter of the crown to be increased.

According to one advantageous embodiment, at least the unfolding element of the crown of the apparatus can be made of shape memory material. The unfolding element can be made of a biocompatible shape memory polymer, for example, or a biocompatible shape memory alloy, such as Nitinol. It is furthermore also possible for the entire apparatus to be made of a shape memory alloy, for example Nitinol. Due to its shape memory properties, the use of a shape memory material such as Nitinol enables a particularly elegant and simple realization of the insertion state and the unfolding of the unfolding element during the transition into the anchoring state. The use of Nitinol as a shape memory material is advantageous, because the Nitinol material is a proven material in the field of medicine, in particular in the field of cardiovascular medicine, for example for heart valve prostheses, stents and vascular prostheses, due to its biocompatibility and the shape memory property, which makes it possible to deliver and place even complex structures, like the apparatus presented here, in a small installation space at the destination.

According to one embodiment, the apparatus can also comprise an arching device having at least one foot. The arching device is designed to unfold during the transition from the insertion state into the anchoring state to position the at least one foot in the blood vessel. By positioning the at least one foot in the blood vessel, the apparatus can be aligned and positioned in the blood vessel, for example, before it is anchored. The arching device can be connected to the crown. Alternatively, the arching device can comprise an arch fixing device for fixing the arching device to the cardiac support system. The apparatus can therefore be configured in one piece if the fixing means, the crown, the connection means and the arching device are coupled to one another, or the apparatus can be in two parts if the arching device is fixed to the cardiac support system by means of its own arch fixing device, and the other components of the apparatus are coupled to one another. The one-piece embodiment can be advantageous with regard to the folding of the apparatus for the insertion state; the two-piece embodiment can be advantageous depending on the design of the cardiac support system. If, for example, the cardiac support system comprises a pump with a motor, a two-part embodiment may provide more flexibility with respect to the installation space of the cardiac support system, for example by allowing the arching device to be fixed to one end of a motor-coupling-pump unit of the cardiac support system and the second part of the apparatus to be fixed to the other end of the motor-coupling-pump unit of the cardiac support system. By means of the arching device, the apparatus can advantageously be aligned and positioned at the destination via the unfolding of the at least one foot. The foot can have an atraumatic shape, for example, so as not to injure the blood vessel during unfolding and in the anchoring state. The arching device can advantageously be designed to enable alignment of the apparatus for the anchoring state when positioning the at least one foot by the configuration of the arching device and the at least one foot.

According to a further embodiment, the arching device can comprise three feet, in particular wherein, for positioning the feet, said feet are formed in a respective cusp of a heart valve. This embodiment is advantageous in terms of being able to position the apparatus and with it the cardiac support system particularly precisely, in particular when the cardiac support system is positioned and anchored behind the aortic valve, for example, by means of the apparatus. The three feet can have a shape adapted to a peanut shape of the cusps, for example, in order to advantageously achieve a particularly advantageous balance between contact surface and torsional rigidity of the three feet.

For a catheter-supported minimally invasive implantation of the cardiac support system connected to the apparatus, it is advantageous if the apparatus is cylindrical in the insertion state as according to one embodiment. For this purpose, the apparatus can, for example be folded. If the apparatus is made of Nitinol, for example, the apparatus can be cut out of a tube and a shape corresponding to the anchoring state can then be embossed by means of a heat treatment. For the insertion state, the apparatus can be folded to correspond to the original cylindrical tube geometry.

It can also be advantageous if the unfolding element has an inclined position in the anchoring state as according to one embodiment. The inclined position can be understood to be a specific angle of the unfolding element relative to the longitudinal axis of the apparatus. In the anchoring state, the unfolding element can be inclined at an angle to support a force-locking connection between the crown and the blood vessel in the anchoring state. The angle relative to the longitudinal axis of the apparatus can be between 20° and 30°, for example, in particular 25°. The inclined position of the unfolding element can advantageously increase the pressing force of the crown on the blood vessel.

According to one embodiment, the crown can comprise a plurality of unfolding elements coupled to one another. Each of the unfolding elements can comprise two unfolding rods connected at their ends and the distance between the two unfolding rods can be smaller in the insertion state than in the anchoring state. The unfolding elements can be coupled to one another by means of a connection to one of the unfolding rods of an adjacent unfolding element. The two unfolding rods can be connected to one another such that, in the anchoring state of the apparatus, each unfolding element forms a rhomb shape with rounded corners in axial direction to the longitudinal axis of the apparatus. Such a configuration of a plurality of rhomb-shaped unfolding elements coupled to one another can correspond to a standard cross-section of a vascular stent, which can be advantageous when producing the apparatus.

According to one embodiment the unfolding element can alternatively comprise a plurality of loops arranged in a meandering manner, wherein the distance between the loops is smaller in the insertion state than in the anchoring state. This embodiment provides a particularly space-saving folding of the apparatus for the insertion state.

According to one embodiment, the connection means can comprise at least one flexure strut. The flexure strut is designed to open during the transition from the insertion state into the anchoring state to allow the crown to unfold. The flexure strut enables a particularly elegant and space-saving connection between the fixing means and the crown. The flexure strut can be made of, for example, an elastic material, for example also Nitinol.

According to a further embodiment, a first end of the flexure strut can furthermore be fastened to the fixing means. A second end of the flexure strut can be fastened to a connection between two adjacent unfolding elements, or the second end of the flexure strut can be fastened to an end of the crown facing away from the fixing means. The flexure strut can thus be configured to correspond to the shape of the unfolding element of the crown to enable efficient unfolding of the crown depending on the embodiment and, depending on the embodiment of the unfolding element, enable compact folding with respect to the axial length of the apparatus for the insertion state.

According to one embodiment, the fixing means can be designed to fix the apparatus in a form-locking and/or force-locking manner to the cardiac support system. The apparatus can thus be connected to the cardiac support system in a stable manner in order to absorb forces that occur, for example, during implantation or during the operating time of the cardiac support system. For this purpose, the fixing means can comprise an element for form-locking engagement, for example, or a recess for receiving an element in a form-locking manner that is disposed on the housing of the cardiac support system, for example. The element for form-locking fixing can have different cross-sections, for example, and the element or the corresponding recess can, for example, be round, oval, triangular, polygonal or star-shaped. For this purpose, both the fixing means and the cardiac support system, for example the housing of the cardiac support system, can comprise elements that enable the fixing means to be snapped into or anchored to the cardiac support system. Additionally or alternatively, the fixing means can, for example, comprise a bayonet connection or a clip connection or a hook. Additionally or alternatively, the fixing means can also be implemented by means of a material-locking connection. The fixing means can, for example, be configured to enable a rotational movement between the apparatus and the cardiac support system.

According to one embodiment, the apparatus can also comprise a sleeve. The sleeve can be movable relative to the crown. The sleeve can furthermore be designed to enclose at least the crown in the insertion state and to release the crown to initiate the transition into the anchoring state. If, as according to one embodiment, the apparatus comprises the arching device, the sleeve can also be movable relative to the arching device and can furthermore be designed to also enclose the arching device in the insertion state and to release the arching device to initiate the transition into the anchoring state. The sleeve can also be designed to enclose and then release all of the other components of the apparatus. The sleeve can be cylindrically shaped, for example, and designed such that the apparatus with the sleeve can be inserted into a commercially available catheter in the insertion state. The sleeve can, for example, advantageously be used to hold down the other components of the apparatus in the folded state of the apparatus and thereby additionally stabilize them in the insertion state; for example also when components of the apparatus or the entire apparatus are made of a shape memory material. The sleeve can furthermore be removed gradually during the transition from the insertion state into the anchoring state, for example via a controlled mechanism that can be controlled electrically, for example, or by manually pulling back the sleeve. The apparatus can thus, for example, be unfolded incrementally to advantageously unfold the apparatus in a controlled manner and position it prior to anchoring, or the sleeve can be moved forward again to realign the apparatus or correct the positioning of the apparatus.

A method for operating the apparatus according to one embodiment is also presented along with this approach. The method comprises at least one unfolding step. In the unfolding step, the unfolding element of the crown of the apparatus is unfolded during the transition from the insertion state into the anchoring state to increase the diameter of the crown. The unfolding step can, for example, also be carried out to increase the diameter of the crown to anchor the apparatus in the blood vessel. The method can be carried out when the apparatus is disposed inside a blood vessel and also when the apparatus is located outside a blood vessel, for example in order to connect the apparatus to a component of an implant by increasing the diameter of the crown.

A production method for producing an apparatus for anchoring a cardiac support system in a blood vessel is presented as well. The apparatus can assume an insertion state for inserting the cardiac support system into the blood vessel, and the apparatus can furthermore assume an anchoring state for anchoring the cardiac support system in the blood vessel. The production method comprises at least one step for providing, one step for forming and one step for heat treating. In the providing step, a semi-finished product made of a shape memory material is provided. In the forming step, a fixing means for fixing the apparatus to the cardiac support system is formed. The forming step also includes forming a crown consisting of at least one unfolding element, wherein the unfolding element is designed to unfold during a transition from the insertion state into the anchoring state in order to increase the diameter of the crown to anchor the apparatus in the blood vessel. Furthermore, in the forming step, a connection means is formed to connect the crown to the connection means. The fixing means, the crown and the connection means are formed from the semi-finished product. In the heat-treating step, the fixing means, the crown and the connection means are heat-treated to emboss the shape of the anchoring state.

A cardiac support system having an apparatus according to an embodiment is presented as well. The apparatus can be fixed to the cardiac support system, for example. The cardiac support system can, for example, comprise a heart pump with a motor-coupling-pump unit. The cardiac support system can furthermore comprise a housing, which is designed to be connected to the apparatus in a form-locking and/or force-locking manner, for example by means of the fixing means of the apparatus. According to this embodiment, the size of the cardiac support system and/or the dimensions of the apparatus can advantageously be selected or changed in a patient-specific manner.

BRIEF DESCRIPTION OF THE DRAWINGS

Design examples of the approach presented here are shown in the drawings and explained in more detail in the following description. The figures show:

FIGS. 4 and 5 a schematic illustration of an insertion state of an apparatus for anchoring a cardiac support system in a blood vessel according to a design example;

DETAILED DESCRIPTION

In the following description of favorable design examples of the present invention, the same or similar reference signs are used for the elements shown in the various figures, which have a similar effect, whereby a repeated description of these elements is omitted.

Figure 1:
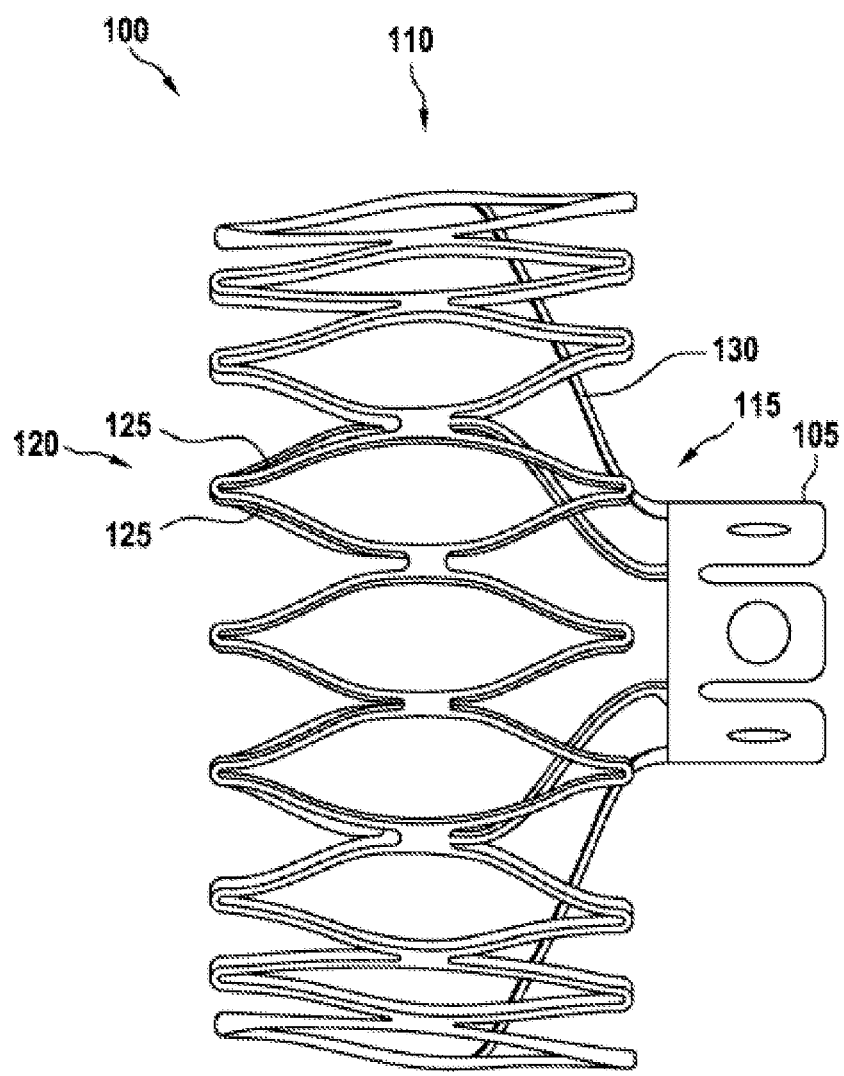
FIG. 1 a schematic illustration of an apparatus for anchoring a cardiac support system in a blood vessel according to a design example.

FIG. 1 shows a schematic illustration of an apparatus 100 for anchoring a cardiac support system in a blood vessel according to a design example. Even if the apparatus 100 is described here and in the following in the context of a cardiac support system, the apparatus 100 can also be used to anchor other implants in a blood vessel.

The figure shows a side view of the unfolded apparatus 100. The apparatus 100 can assume an insertion state for inserting the cardiac support system into the blood vessel. The apparatus 100 can also assume the anchoring state shown in FIG. 1 to anchor the cardiac support system in the blood vessel.

The apparatus 100 comprises at least one fixing means 105 for fixing the apparatus 100 to the cardiac support system, a crown 110 and a connection means 115. The crown 110 consists of at least one unfolding element 120. The unfolding element 120 is designed to unfold during a transition from the insertion state into the anchoring state in order to increase the diameter of the crown 110 to anchor the apparatus 100 in the blood vessel. According to the shown design example, the crown 110 comprises a plurality of unfolding elements 120. The connection means 115 is designed to connect the crown 110 to the fixing means 105.

The apparatus 100 can advantageously be used to prevent the cardiac support system from shifting or moving, because the crown 110 can be used to anchor the apparatus at the implantation site. The apparatus 100 can furthermore enable a defined positioning of the cardiac support system, which is also mentioned in the following. The apparatus can be made at least partially of a shape memory material such as Nitinol. In FIG. 1 shown here, the apparatus 100 is configured as a Nitinol frame for anchoring and positioning a cardiac support system in a blood vessel. The apparatus 100 can have a design for long-term use as well as a retrievable design for short-term implantations, for example via a controlled transitioning of the implanted and anchored apparatus 100 from the anchoring state into the insertion state.

The crown 110 and the fixing means 105 of the apparatus 100 extend along a longitudinal axis of the apparatus 100, which can correspond to the axis of a catheter in which the cardiac support system is inserted via the leg artery in a minimally invasive manner.

In the illustration shown here, the unfolding element 120 and with it the crown 110 is unfolded in accordance with the anchoring state. According to the shown design example, the unfolding element 120 can have an inclined position relative to the longitudinal axis of the apparatus 100 in the anchoring state. The unfolding element 120 can be inclined at a specific angle, for example a 250 angle, in order to produce an increased pressing force of the crown 110 for the force-locking anchoring of the apparatus 100 in the blood vessel.

As in the design example shown here, the crown 110 can comprise a plurality of unfolding elements 120 coupled to one another, wherein each of the unfolding elements 120 comprises two unfolding rods 125 connected at their ends. The distance between central sections of the two unfolding rods 125 of each unfolding element 120 is smaller in the insertion state than in the anchoring state. According to this design example, the central sections of all unfolding elements 120 are arranged on a circular path. In the unfolded state, each unfolding element 120 can have a rhomb shape with rounded corners, wherein the rhomb shape is configured by removing the two unfolding rods 125 connected at their ends. The unfolding elements 120 coupled to each other form a grid-like ring. The unfolding elements 120 can be identically shaped.

The connection means 115 optionally comprises at least one flexure strut 130. The flexure strut 130 is designed to open during the transition from the insertion state into the anchoring state to allow the crown 110 to unfold. The connection means 115 can also comprise a plurality of flexure struts 130, for example to enable a particularly uniform unfolding of the unfolding element 120 and thus of the crown 110. As an example, in the design example shown here, the apparatus 100 comprises four equally spaced flexure struts 130.

According to a design example, a first end of the flexure strut 130 is fastened to the fixing means 105 and, as shown here, a second end of the flexure strut 130 is fastened to a connection between two adjacent unfolding elements 120. The second end of the flexure strut 130 can alternatively be fastened to an end of the crown 110 facing away from the fixing means 105.

According to a design example, the fixing means 105 is designed to fix the apparatus 100 in a form-locking and/or force-locking manner to the cardiac support system. For this purpose, the fixing means 105 can, for example as shown here, comprise a recess for receiving a disposing element in a form-locking manner, wherein the corresponding element can be formed in a component of the cardiac support system to be fixed.

According to a design example, the fixing means 105 is shaped as a ring comprising a plurality of recesses. In the unfolded state of the crown 110, the ring-shaped crown 110 has a larger diameter than the ring-shaped fixing means 105.

According to a design example, the crown 110 and the fixing means 105 do not overlap or overlap only slightly.

According to a design example, a longitudinal axis of the apparatus 100 extends centrally through the crown 110 and the fixing means 105. According to a design example, the unfolding elements 120 have an inclined position in the unfolded state, wherein the ends of the unfolding elements 120 facing the fixing means 105 are further away from the longitudinal axis of the apparatus 100 than the ends of the unfolding elements 120 facing away from the fixing means 105.

Figure 2:
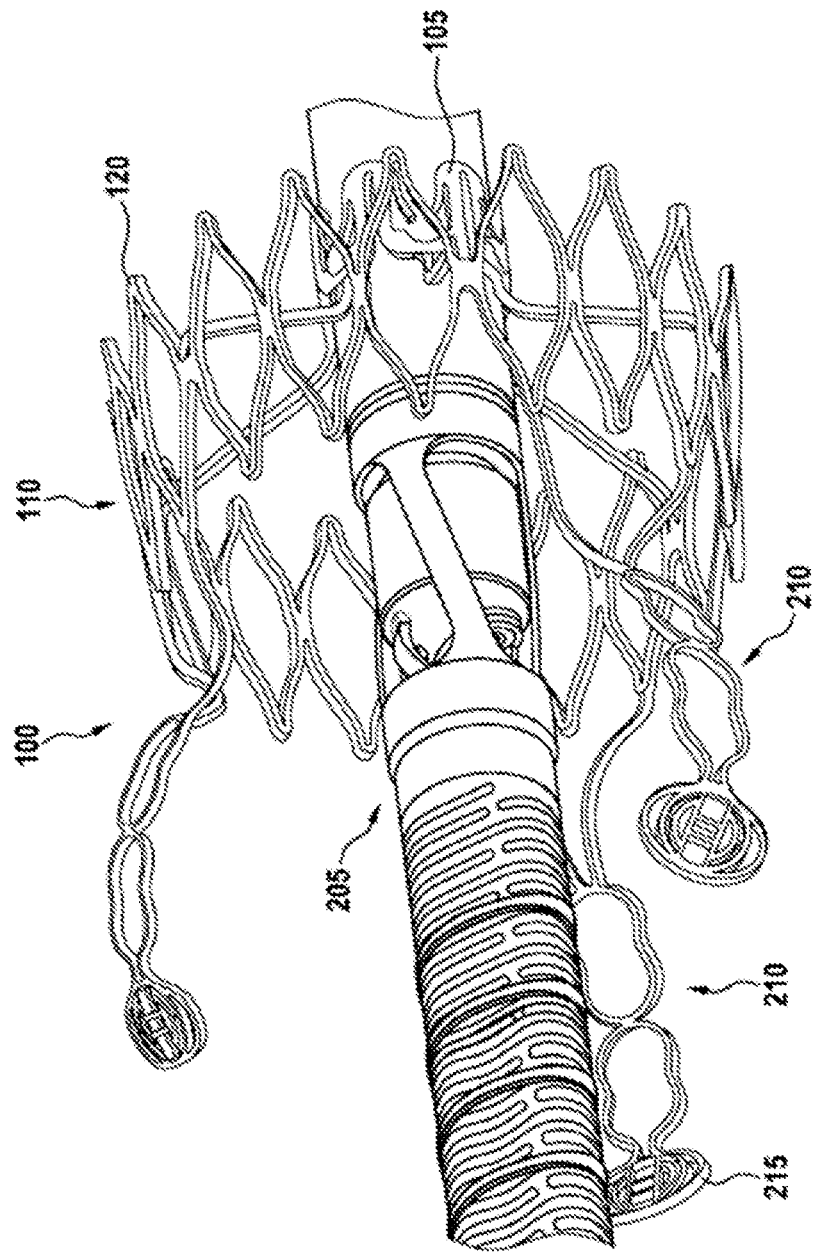
FIG. 2 a schematic illustration of a part of a cardiac support system with an apparatus for anchoring a cardiac support system in a blood vessel according to a design example.

FIG. 2 shows a schematic illustration of a part of a cardiac support system 205 with an apparatus 100 for anchoring the cardiac support system 205 in a blood vessel according to a design example. A section of a heart pump having tube-shaped components, which include a motor and an impeller of the heart pump, is shown as an example of a part of the cardiac support system 205. In the plan view shown here, the apparatus 100 is fixed to a housing section of the cardiac support system 205.

According to a design example, the unfolding element 120 can be made of a shape memory material. It is also possible for multiple components, or the apparatus 100 as a whole, to be made of a shape memory material, for example Nitinol as shown here.

According to the design example shown here, the apparatus 100 comprises an arching device 210 having at least one foot 215. The arching device 210 is designed to unfold during the transition from the insertion state into the anchoring state and thus enable the positioning of the at least one foot 215 in the blood vessel. The arching device 210 here is connected to the crown 110. The arching device 210 can alternatively also comprise an arch fixing device for fixing the arching device 210 to the cardiac support system 205; this is shown in FIG. 3 below.

The arching device 210 can comprise three feet 215, as shown here. To position the feet 215, the feet 215 can in particular be formed in a cusp of a heart valve, for example when the cardiac support system 205 fixed by the apparatus 100 is positioned and anchored inside a human aorta directly behind an aortic valve.

The fixing means 105 can fix the apparatus 100 to the cardiac support system by means of a form-locking, force-locking or material-locking connection mechanism. For this purpose, as shown here for example, the cardiac support system 205 can comprise a connection element for form-locking engagement of the fixing means 105, and the fixing means 105 can comprise a corresponding material recess for engagement or a correspondingly formed connection element for engagement, such as the clip connection shown here. The cardiac support system 205 can thus be fixed to the apparatus 100 to anchor the cardiac support system 205 in the blood vessel, for example in the aorta. The crown 110 ensures that the cardiac support system 205 is held in the aorta by a radial frictional connection of the apparatus with a wall section of the aorta.

Figure 3:
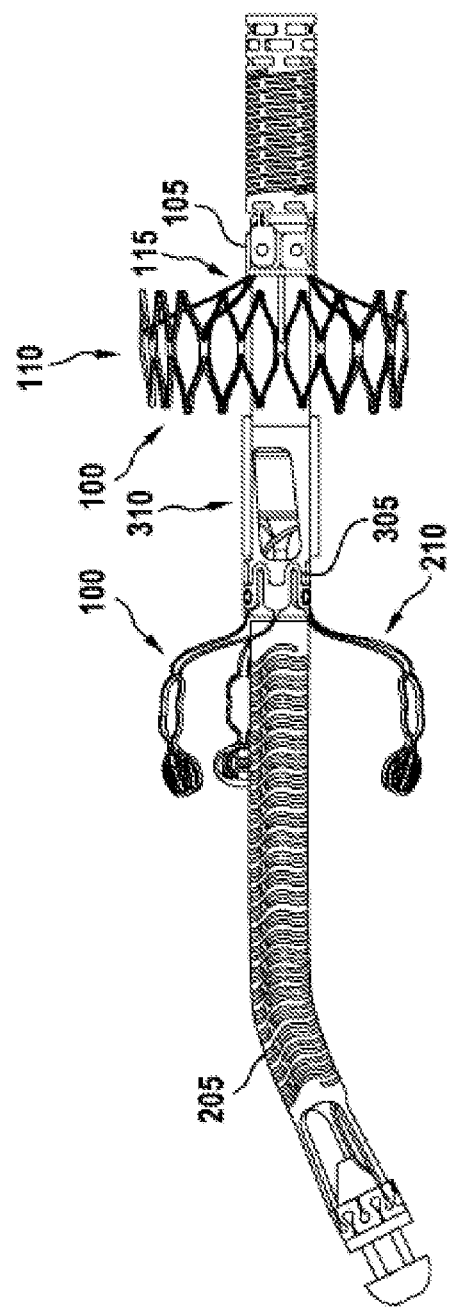
FIG. 3 a schematic illustration of a cardiac support system with an apparatus for anchoring a cardiac support system in a blood vessel according to a design example.

FIG. 3 shows a schematic illustration of a cardiac support system 205 with an apparatus 100 for anchoring a cardiac support system 205 in a blood vessel according to a design example. The figure shows a side view of the cardiac support system 205 with the apparatus 100, whereby the apparatus 100 is configured in two parts. One part of the apparatus 100 comprises the crown 110 which is connected to the fixing means 105 by the connection means 115, and another part of the apparatus 100 consists of the arching device 210. The apparatus 100 is in an unfolded state corresponding to the anchoring state.

According to the design example shown here, the arching device 210 comprises an arch fixing device 305 for fixing the arching device 210 to the cardiac support system 205 and is not connected to the crown 110. As shown here as an example, the arch fixing device 305 can fix the arching device 210 to the cardiac support system 205 by means of a form-locking and force-locking connection.

The insertion of the cardiac support system 205, such as the heart pump shown here as an example, can preferably be performed in a minimally invasive manner through a human leg artery, the femoral artery. The insertion diameter available for the components of the apparatus 100 can likewise be limited by the maximum diameter of the femoral artery in the region of the implantation site or of other arteries over the course (for example the iliac artery, etc.) or even, for example, by the tortuosity or the degree of calcification of the arterial flow path. The cardiac support system 205 and the apparatus 100, which can be brought into the body in this way, can consequently be limited in terms of diameter and overall length. In the case of a heart pump as the cardiac support system 205, a high speed of the motor and the pump wheel of the heart pump can be set to nonetheless achieve significant support of the heart. The miniaturization of these components of the heart pump in combination with the high speed can lead to a decrease in the efficiency of the electric motor and an increase in the surface temperature as a result of the small heat-dissipating surface. If the apparatus 100 comprises an arching device 120 and is designed in one piece according to one embodiment as shown in the previous FIG. 2, the apparatus can fit snugly against the tube-shaped components of the cardiac support system 205 in the insertion state in order to keep the diameter as small as possible. The folded one-piece apparatus 100 can extend over the entire length of the motor-coupling-pump unit of the cardiac support system 205. In this case, a two-part apparatus such as the design example shown in the present FIG. 3 is advantageous: A two-part design of the apparatus 100 and with it also a two-part anchoring of the cardiac support system 205 in the body makes it possible to save radial installation space in the region of the motor and impeller of the heart pump, for example in the region 310 of the cardiac support system 205 identified here. The installation space gained in this way in the region 310 can be used to enlarge the pump rotor of the cardiac support system 205, for example, and thus reduce the speed in order to improve the efficiency. Or the diameter of the diameter of the coupling between the motor and the pump rotor of the cardiac support system 205 can be increased in the region 310 in order to be able to transmit a higher torque, or to save overall length of the coupling of the cardiac support system 205. The region 310 can also be used to attach flow guiding geometries, for example guide vanes, to the housing of the cardiac support system 205 in order to thus increase the efficiency and to calm the blood flow.

FIG. 4 shows a schematic illustration of an insertion state of an apparatus 100 for anchoring a cardiac support system 205 in a blood vessel according to a design example in a side view. The apparatus 100 here comprises a sleeve 405, into which the cardiac support system 205 is inserted. The cardiac support system 205 is also connected to the apparatus 100 by means of the fixing means 105, and the connection means 115 connects the crown 110 to the fixing means 105. The crown 110 is connected to the arching device 210.

According to the design example shown here, the apparatus 100 is cylindrical in the insertion state. For this purpose, the connection means 115, the crown 110 and the arching device 210 are folded together in a cylindrical manner; all of the components of the apparatus rest against the cardiac support system 205 and/or one respective other component of the apparatus 100.

The unfolding element, of which the crown 110 is configured, is optionally made of a shape memory material, for example Nitinol. Other components of the apparatus, such as the arching device 210 and the connection means 115, can likewise be made of a shape memory material. If, for example, the crown 110, the connection means 115, and the arching device 210 are cut out of a Nitinol tube, said components can be folded to their original cylindrical shape, the tube geometry, for the implantation process, due to the pseudoelastic properties of the shape memory material. The small installation space thus makes catheter-supported minimally invasive implantation possible. If the apparatus 100 comprises a sleeve 405 as in this case, the connection means 115, the crown 110 and the arching device 210 can be held down by the sleeve 405 and thus additionally or alternatively prevented from unfolding. In the illustration shown here, the aforementioned components of the apparatus 100, the crown 110, the connection means 115 and the arching device 210, are accordingly shown in the folded state inside the sleeve 405.

If the apparatus 100 comprises the sleeve 405 as according to a design example, the sleeve 405 is movable relative to the crown 110. The sleeve 405 is furthermore designed to enclose at least the crown 110 in the insertion state and to release at least the crown 110 to initiate the transition into the anchoring state. The sleeve 405 can thus be used to hold down the crown 110 and the arching device 210 in particular during the implantation process, so that these components do not unfold and thus do not stand up. For this purpose, the sleeve 405, also referred to as the release sheath, is pushed into a catheter over the other components of the apparatus 100 when the cardiac support system 205 connected to the fixing means 105 of the apparatus 100 is loaded into a catheter. As soon as the final position of the cardiac support system 205, e.g. in front of the heart valve, is reached, the sleeve 405 is pulled back, so that the crown 110 and the arching device 210 can unfold. Until then, the surgeon can reversibly determine the axial position, the rotational alignment and the position of the suction hose of the cardiac support system 205 in the ventricle. The sleeve 405 can furthermore be pulled back incrementally, so that there is a slow, gradual release of the arching device 210 and the crown 110 during the transition from the insertion state into the anchoring state.

FIG. 5 shows a schematic illustration of an insertion state of an apparatus 100 for anchoring a cardiac support system 205 in a blood vessel according to a design example. The figure shows a sectional view of the side view shown in the previous FIG. 4. The arching device 210 and the crown 110 are therefore in the loaded state and, together with the connection means and the fixing means 105, are enclosed by the sleeve 405, into which the cardiac support system 205 fixed to the apparatus 100 is inserted. The loaded state shown here makes it difficult to distinguish the components of the apparatus 100 inside the sleeve 405 from the cardiac support system 205, because they are in close contact with the cardiac support system 205. This illustrates the possibility of folding the apparatus 100 in a such a way that the cardiac support system 205 fixed to the apparatus direction 100 can be inserted and implanted in a minimally invasive manner.

Figure 6:
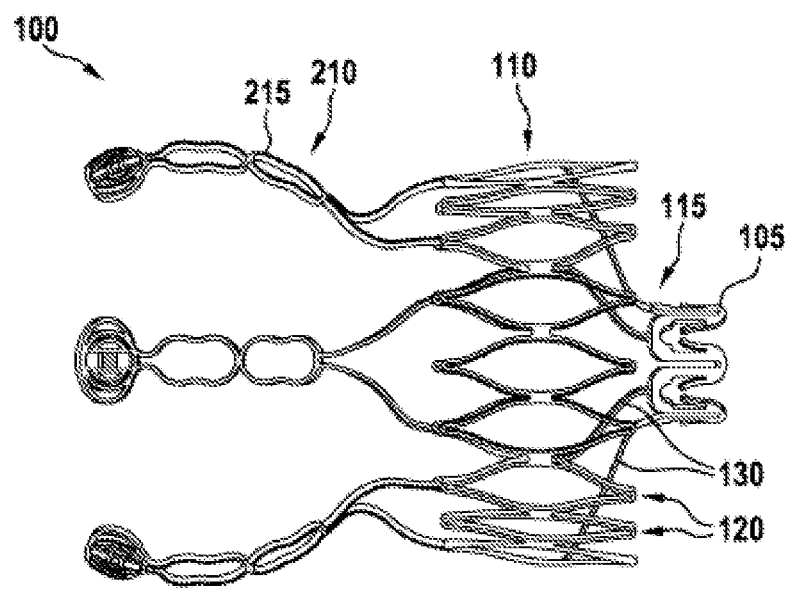
FIG. 6 a schematic illustration of an apparatus for anchoring a cardiac support system in a blood vessel having an arching device according to a design example.

FIG. 6 shows a schematic illustration of an apparatus 100 for anchoring a cardiac support system in a blood vessel having an arching device 210 according to a design example. The figure shows a side view of the apparatus 100 in the unfolded state in a one-piece design. The fixing means 105 comprises the configuration and the recesses for form-locking engagement in an element disposed on the cardiac support system by means of a clip connection. The connection means 115 here consists of four flexure struts 130 respectively connected at one end to the fixing means 105. The crown 110 consists of a plurality of unfolding elements 120 coupled to one another, the respective unfolding rods of which form rhombs. The respective other end of the four flexure struts 130 of the connection means 115 is connected to a connection of two adjacent unfolding elements 120. The arching device 210 is connected to the crown 110 at the end of the crown 110 opposite to the fixing means 105. The arching device 210 here comprises three feet 215. The feet 215 are respectively initially bent in a trough-shaped manner in the direction of the longitudinal axis of the apparatus 100 in one of their sections adjacent to the connection to the crown 110, and then form a semicircular arc in a section longer than half the length of each foot 215.

The crown 110 shown here can have an outer diameter in the unfolded state for anchoring the cardiac support system that is slightly larger than a human aorta, for example, so as to enable a uniform frictional connection to the blood vessel in the form of said aorta; the outer diameter in this case can be 20-30 mm, for example. The pressing force of the crown 110 and with it also the apparatus 100 is produced by the webs in the form of the unfolding elements 120, which are inclined at an angle of 20°-30°, in particular approx. 25°. The crown 110 advantageously has a conical shape with a 5°-10° angle which can ensure a continuous tangential connection to the release sheath in the form of the sleeve during the release process, i.e. during the transition from the insertion state into the anchoring state, and consequently a controlled release behavior, i.e. a controlled unfolding of the crown 110 and the arching device 210. The crown 110 has a length of 10-15 mm, in particular 13 mm. The fixing means 105 enables a connection to the cardiac support system, for example to a heart pump, via a connection to the motor housing of the cardiac support system. The rhomb shape of the unfolding elements 120 shown here represents a standard cross-section for vascular stents and makes a laser cut from a tube possible. The feet 215 of the arching device 210 respectively have an axial length of 20-30 mm, in particular 24 mm. At the front, i.e. at the end of the feet 215 opposite to the crown, the arching device 210 has a rotation diameter of 20-30 mm, in particular 23 mm, adapted to a human aortic valve. The feet 215 furthermore have an atraumatic shape, so that the aortic wall is not injured when the feet 215 are inserted and unfolded and the feet 215 can slide automatically into the cusps of the aortic valve. This anchoring shape of the feet 215 is advantageous, because the peanut shape of the cusps provides a particularly advantageous balance between contact surface and torsional rigidity. The indentation of the arching device 210 at the beginning of the feet 215, i.e. at the distal end connected to the crown 110, is designed such that, in the event of a partial release during the transition from the insertion state into the anchoring state, i.e. when the crown 110 is still in the crimped state, the target outer diameter of the arching device 210, which corresponds to the rotation diameter, has already been reached.

The frame of the apparatus 100 consisting of the fixing means 105, the connection means 115, the crown 110 and the arching device 210 can, for example, be produced by means of the production method presented here using a shape memory material. For this purpose, an elastic material, preferably Nitinol or another shape memory alloy, is used for the frame. A tube geometry having the desired wall thickness of the later construction elements, the crown 110, the feet 215 of the arching device 210, the connection means 115 and the fixing means 105, is a suitable semi-finished product for processing. The construction elements are realized using a method for material removal, preferably laser cutting, by removing pipe volume at the not needed locations. Punching and erosion methods or machining are alternatively possible as well. The laser-cut contour can now be brought into the desired shape, for example the shape shown here, as a part of a heat treatment, for example at a temperature above 500° C. The embossing process is a plastic deformation without the occurrence of material failure. The shape embossed in this way is then set automatically as soon as the transformation temperature is exceeded. This can be set via the alloy ratio and, in the application described, can be below body temperature, preferably between 0° C. and 10° C. To be able to serve patient groups having different sizes, the Nitinol frame of the apparatus 100 formed in this way can be made available in different sizes. For this purpose, the fixing of the apparatus 100 with the cardiac support system can, for example, take place right before loading the implantation device with which the cardiac support system connected to the apparatus 100 can be inserted. This allows the correct, patient-specific size of the crown 110 and the feet 215 to be selected shortly before implantation. When the cardiac support system is used for a longer period of time, the Nitinol structure of the frame allows it to grow together with the aorta, as the body's own tissue covers the biocompatible material.

Figure 7:
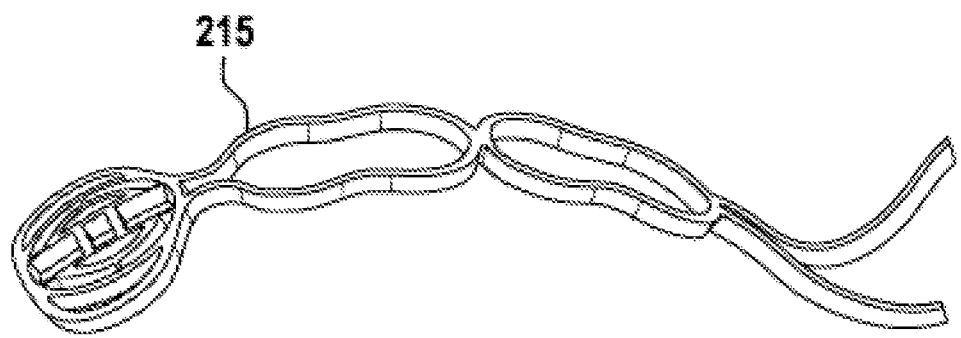
FIG. 7 a schematic illustration of a foot of an apparatus for anchoring a cardiac support system in a blood vessel according to a design example.

FIG. 7 shows a schematic illustration of a foot 215 of an arching device according to a design example. The figure shows a plan view of the foot 215 of the arching device of the apparatus. The foot shown here corresponds to the uppermost foot 215 in the preceding FIG. 6, with the described arc-shaped short indentation followed by a semicircular bulge, wherein the bulge does not represent an exact semicircle, but rather a flatter semicircular arc section. The arc shape of the foot can correspond to the form of a section of a human heart valve, for example a cusp of the aortic valve. During the transition of the apparatus from the insertion state into the anchoring state, the foot 215 can unfold first. The foot 215 can then be positioned to align the cardiac support system in the blood vessel, for example behind the heart valve in the cusps of the aortic valve. If the desired positioning is not immediately successful, the feet 215 can also be folded again, even repeatedly, for example using the sleeve, by sliding the sleeve forward again, i.e. over the feet 215, and then sliding it back to reposition the feet 215 and thus allowing the feet 215 to unfold.

Figure 8:
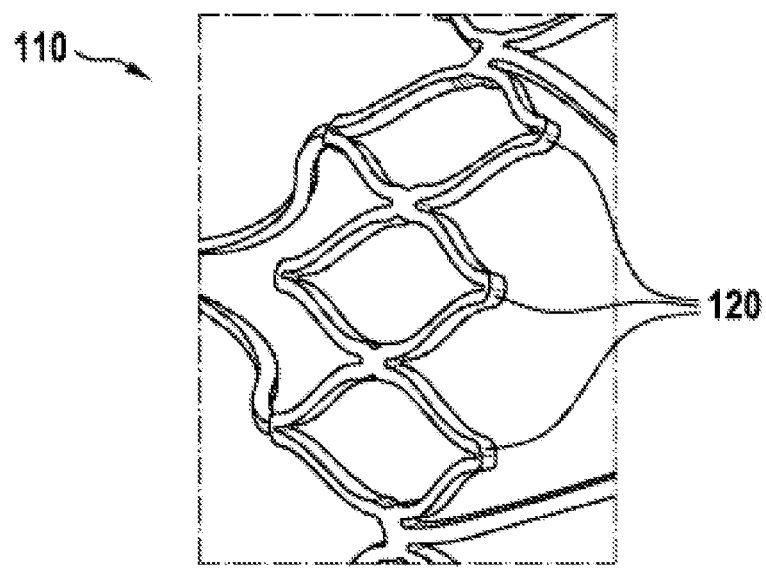
FIG. 8 a schematic illustration of a part of a crown of an apparatus for anchoring a cardiac support system in a blood vessel according to a design example.

FIG. 8 shows a schematic illustration of a part of a crown 110 of an apparatus for anchoring a cardiac support system in a blood vessel according to a design example. As a section of the crown 110, the figure shows a plan view onto three unfolding elements 120 of the crown 110, which are unfolded into a rhomb shape, in a conical configuration of the crown 110. The sectional contour of the crown 110 shown here corresponds to the not perfectly circular aortic anatomy of the human aorta.

During the transition of the apparatus from the insertion state into the anchoring state, for example, the arching device can be unfolded first and then the crown 110. The shape of the crown in the unfolded state, as shown here, can be such that a uniform force-locking connection is created between the crown 110 and the aorta. This connection allows the cardiac support system to be held in position, and the resulting anchoring of the cardiac support system in the blood vessel prevents dislocation of the cardiac support system during operation. For this purpose, the outer diameter of the crown 110 in the unfolded state of the crown 110 is slightly larger than the inner diameter of the aorta.

Figure 9:
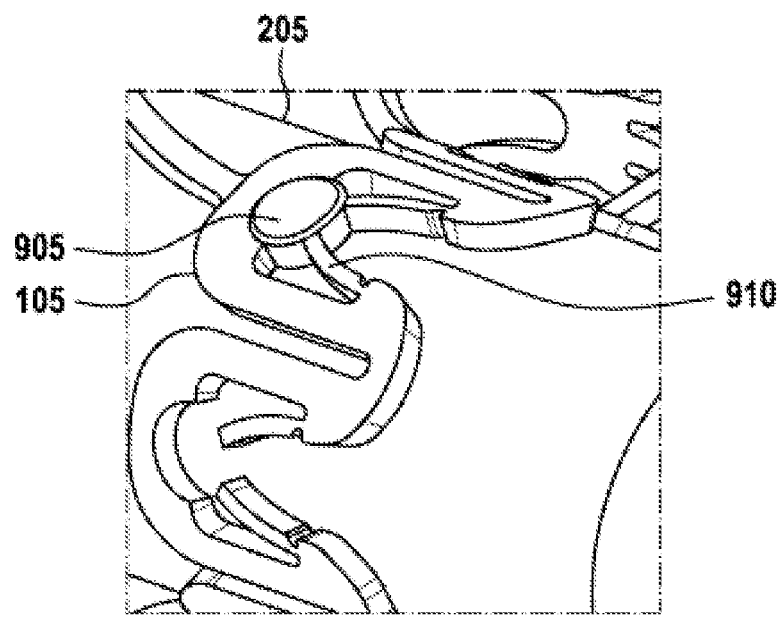
FIGS. 9 and 10 a schematic illustration of a fixing means of an apparatus for anchoring a cardiac support system in a blood vessel according to a design example.

FIG. 9 shows a schematic illustration of a fixing means 105 of an apparatus for anchoring a cardiac support system 205 in a blood vessel according to a design example. The plan view shows the section of the cardiac support system 205 connected to the fixing means 105. According to a design example, the fixing means 105 is designed to fix the apparatus in a form-locking and/or force-locking manner to the cardiac support system 205. The fixing can also be realized in a material-locking manner. The attachment by means of the fixing means 105 can be configured such that the apparatus cannot be detached from the cardiac support system 205 during operation of the cardiac support system 205 and the attachment can remain stable over the operating time of the cardiac support system 205. The fixing means 105 can further be configured to absorb forces occurring during operation of the cardiac support system 205 or during the surgical procedure. The fixing means 105 can be designed to support the positioning of the cardiac support system in the blood vessel. The relative position of the cardiac support system 205 and the fixing means can be adjustable via a rotational movement in both directions and can be designed to be incrementally variable over 360°, and the fixing means 105 and the cardiac support system 205 can consequently be movable relative to one another prior to the form-locking fixing.

For form-locking and/or force-locking fixing of the cardiac support system 205 according to a design example, the fixing means 105 and the cardiac support system 205 can have features that allow the cardiac support system to snap into the apparatus and thus enable an anchoring of the cardiac support system 205 to the apparatus. For this purpose, the cardiac support system 205 and/or the fixing means 105 can comprise at least one disposed element 905 for a form-locking connection of the apparatus and the cardiac support system 205 by means of the fixing means 105. In FIG. 9 here, as an example, the element is disposed on the cardiac support system, is round and has an undercut in cross-section for engagement with the clip connection of the fixing means 105 shown here, which is formed to correspond to the element 905. The clip connection here comprises two locking springs 910 in order to be able to easily connect the fixing means to the cardiac support system, and to achieve additional fixing by means of the locking springs 910 after the engagement of the form-locking element. A latching of the fixing means to the cardiac support system 205, which is configured here in the form of the locking springs 910, can be realized irrespective of the rotational offset of the disposed element 905 relative to the corresponding recess.

The following FIGS. 10 to 17 show various design examples for form-locking and/or force-locking fixing of the cardiac support system 205 to the apparatus.

Figure 10:
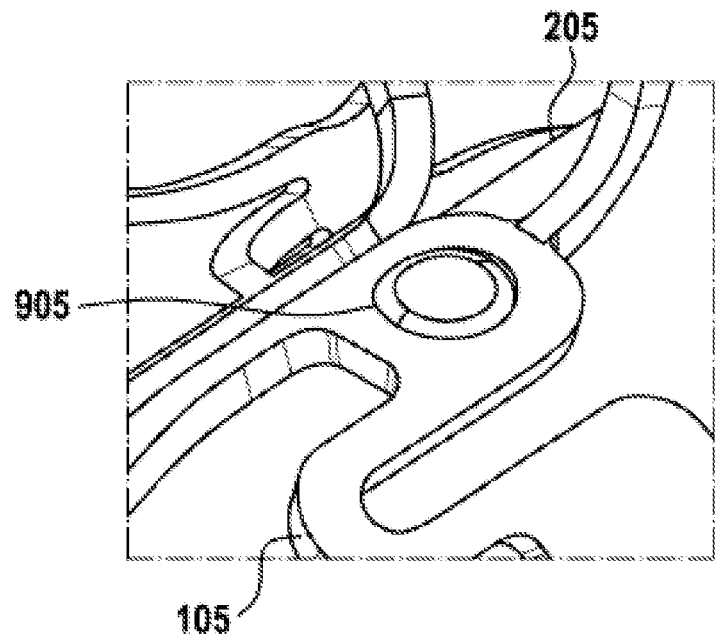

FIG. 10 shows a schematic illustration of a fixing means 105 of an apparatus for anchoring a cardiac support system 205 in a blood vessel according to a design example. The plan view shows a section of the cardiac support system 205 connected to a section of the fixing means 105. A round element 905 is disposed on the cardiac support system, and a section of the fixing means comprises a recess corresponding to the element 905 for form-locking engagement of the fixing means 105 to securely fix the cardiac support system 205 to the apparatus.

Figure 11A:
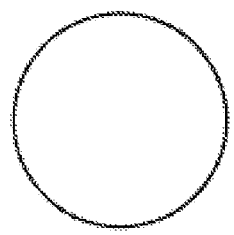
FIGS. 11a to 11j a schematic illustration of a design of a form-locking fixing of an apparatus for anchoring a cardiac support system in a blood vessel according to a design example.
Figure 11B:
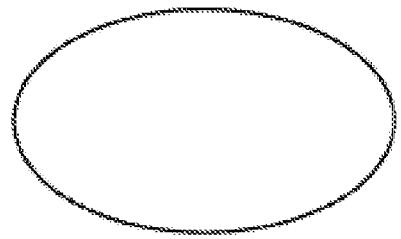
Figure 11C:
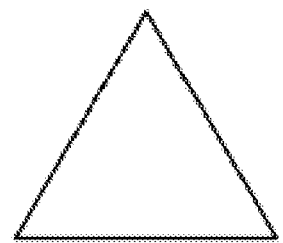
Figure 11D:
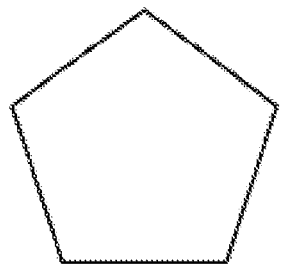
Figure 11E:
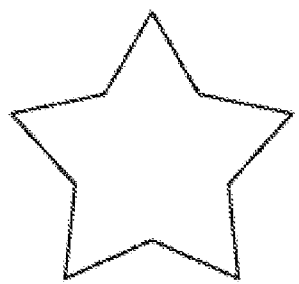
Figure 11F:
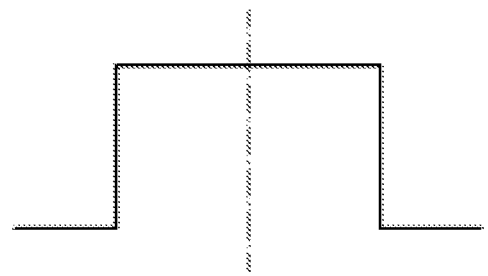
Figure 11G:
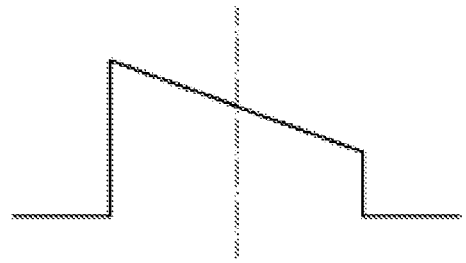
Figure 11H:
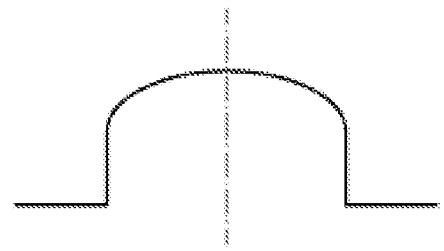
Figure 11I:
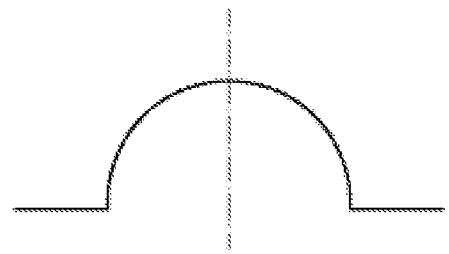
Figure 11J:
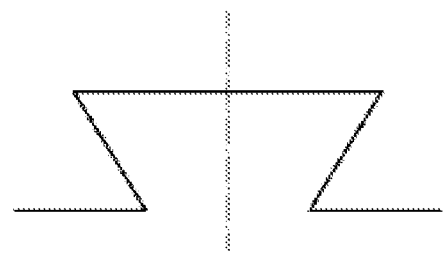

FIGS. 11a to 11j respectively show a schematic illustration of a design of a form-locking fixing of an apparatus for anchoring a cardiac support system in a blood vessel according to a design example. The figure shows a possible configuration of the disposed element shown in the two preceding FIGS. 9 and 10 for form-locking connection of the cardiac support system to the apparatus by means of the engagement of the disposed element and a corresponding recess or configuration as a counterpart. In the manner of a positive and negative design, such a disposing element for form-locking fixing can be realized on both the cardiac support system, for example the housing of the pump, and on the connection mechanism of the apparatus, i.e. on the fixing means. FIGS. 11a to 11e show the various shapes that the element for form-locking fixing can assume as a result of the configuration in a schematic plan view, and FIGS. 11f to 11j show the various cross-sections that such an element can have. The element can be shaped as a circle according to the shape shown in FIG. 11a, or have an oval shape according to the shape shown in FIG. 11b. According to FIG. 11c, the element can be a triangle, or a polygon as shown in FIG. 11d. The element can also be shaped as a star as shown in FIG. 11e. The element can have a rectangular cross-section as shown in FIG. 11f, or the flattening of the cross-section shown in FIG. 11g, the rounding of the cross-section shown in FIG. 11h, the semicircle of the cross-section shown in FIG. 11i, or the undercut of the cross-section shown in FIG. 11j. Combinations of the shown shapes can also be used to shape the element.

Figure 12:
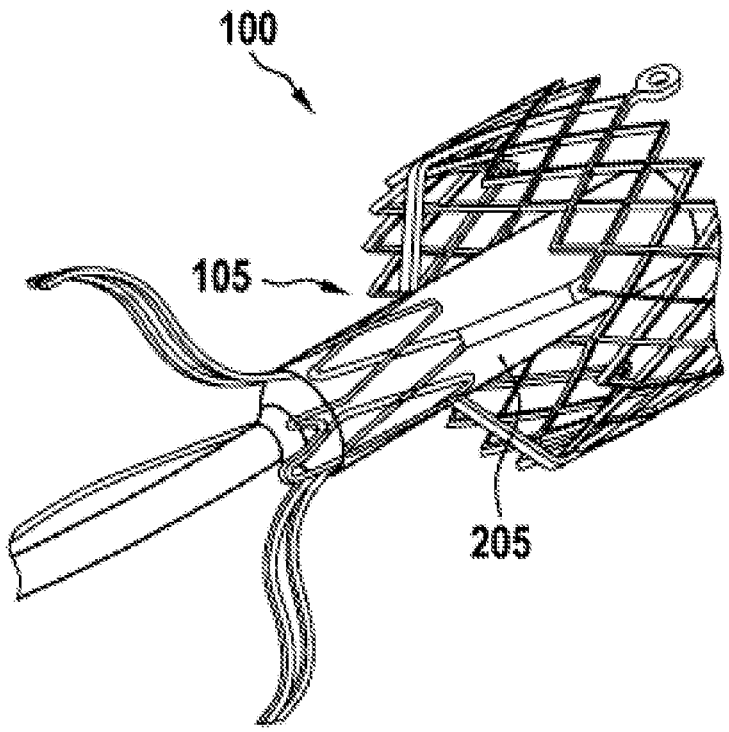
FIG. 12 a schematic illustration of a force-locking fixing of an apparatus for anchoring a cardiac support system in a blood vessel to a cardiac support system according to a design example.

FIG. 12 shows a schematic illustration of a force-locking fixing of an apparatus 100 for anchoring a cardiac support system 205 in a blood vessel to a cardiac support system 205 according to a design example. The plan view shows a section of the cardiac support system 205 and the fixed apparatus 100. The apparatus 100 comprises a fixing means having a plurality of rhomb-shaped fixing elements, which are configured to prevent the heart support system 205 and the apparatus 100 from shifting relative to one another. For this purpose, according to the design example shown here, the fixing elements rest on a section of the cardiac support system 205 and clamp the apparatus against the cardiac support system 205 to fix the apparatus in a force-locking manner to the cardiac support system 205.

Figure 13:
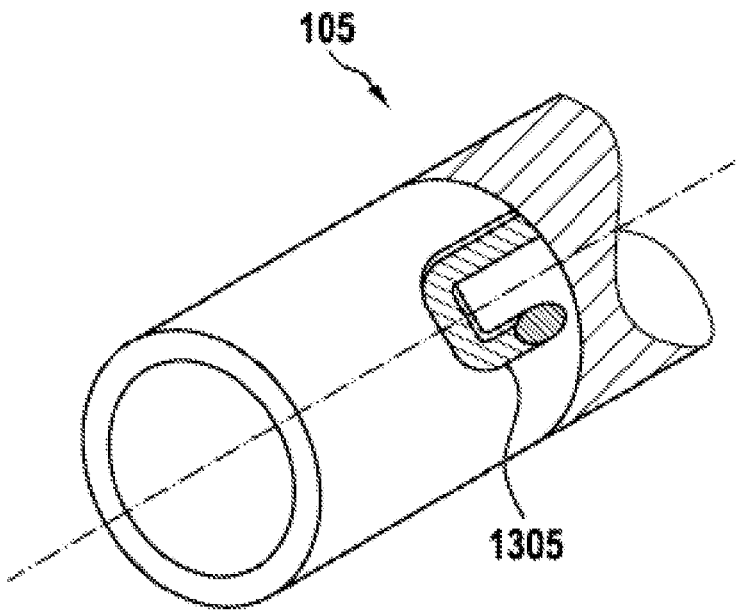
FIG. 13 to 17 a schematic illustration of a part of a fixing means of an apparatus for anchoring a cardiac support system in a blood vessel according to a design example.

FIG. 13 shows a schematic illustration of a part of a fixing means 105 of an apparatus for anchoring a cardiac support system in a blood vessel according to a design example. The figure shows a plan view onto a connection of the apparatus to the cardiac support system, which is realized in a form-locking manner as a bayonet connection. In this case, the fixing means 105 comprises a bayonet connection in the form of a hook.

Figure 14:
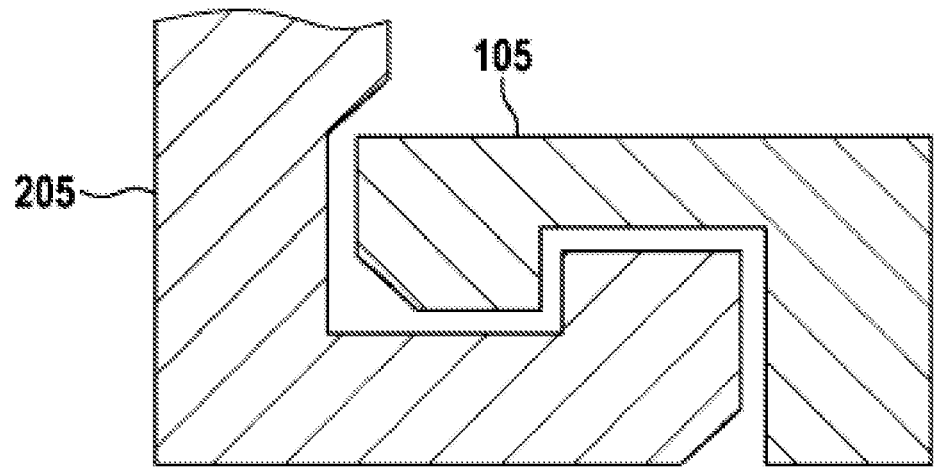

FIG. 14 shows a schematic illustration of a part of a fixing means of an apparatus for anchoring a cardiac support system 205 in a blood vessel according to a design example in cross-section. The fixing means 105 here is configured for form-locking fixing, the cardiac support system comprises a corresponding configuration. The fixing means and the cardiac support system respectively comprise a groove for fixing.

Figure 15:
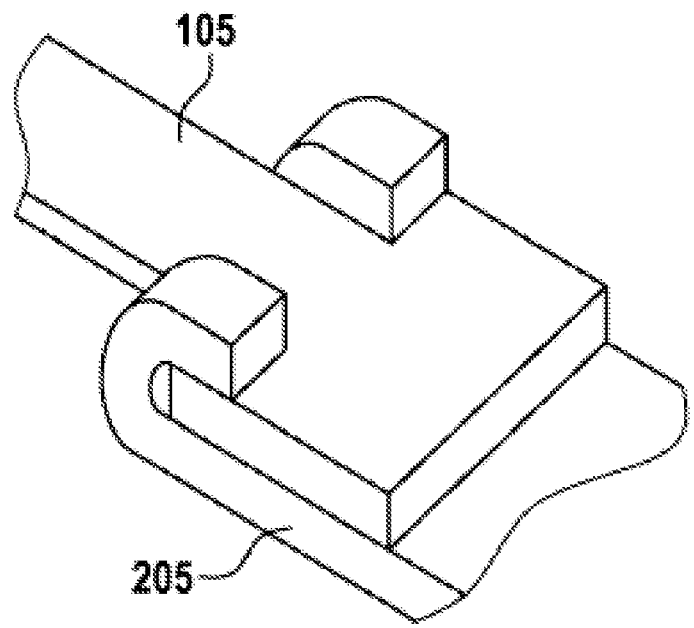

FIG. 15 shows a schematic illustration of a part of a fixing means 105 of an apparatus for anchoring a cardiac support system 205 in a blood vessel according to a design example. The figure shows a section of the fixing means 105 and a section of the cardiac support system 205 as examples, whereby the sections engage in one another in a form-locking manner. The plan view shows the form-locking connection of the fixing means 105 to the cardiac support system via an engagement of the fixing means 105 in two hooks of the cardiac support system 205.

Figure 16:
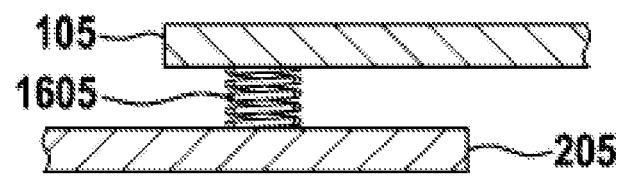
Figure 16:
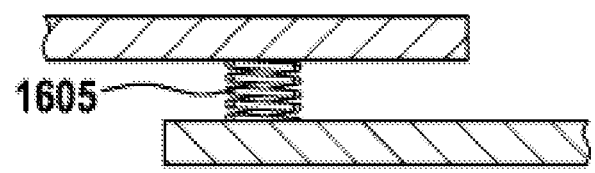

FIG. 16 shows a schematic illustration of a part of a fixing means of an apparatus for anchoring a cardiac support system 205 in a blood vessel according to a design example. The figure shows a cross-section of a force-locking connection of the cardiac support system 205 to the fixing means 105, which is realized here as a spring clamp via a spring connection using two springs 1605 between the heart support system 205 and the fixation device 105.

Figure 17:
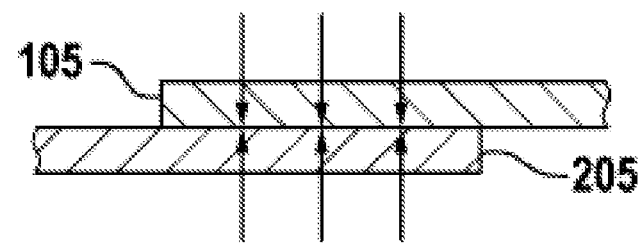
Figure 17:
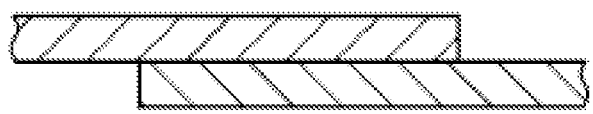

FIG. 17 shows a schematic illustration of a part of a fixing means of an apparatus for anchoring a cardiac support system 205 in a blood vessel according to a design example. The figure shows a cross-section of a press connection as the force-locking connection of the cardiac support system 205 to the fixing means 105. The assembly of the press connection shown here can be produced with the aid of a pressing force, or with the aid of a temperature difference between the cardiac support system 205 and the fixing means 105, i.e. by press joining with the aid of a temperature difference between the fixing means 105 and the cardiac support system 205 and the pressure that occurs during the subsequent temperature compensation.

Figure 18A:
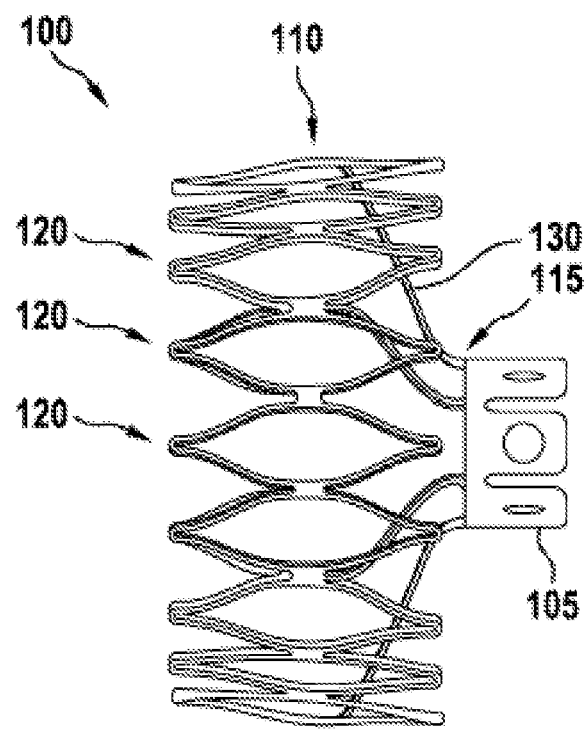
FIG. 18a to 18c a schematic illustration of an apparatus for anchoring a cardiac support system in a blood vessel according to a design example.
Figure 18B:
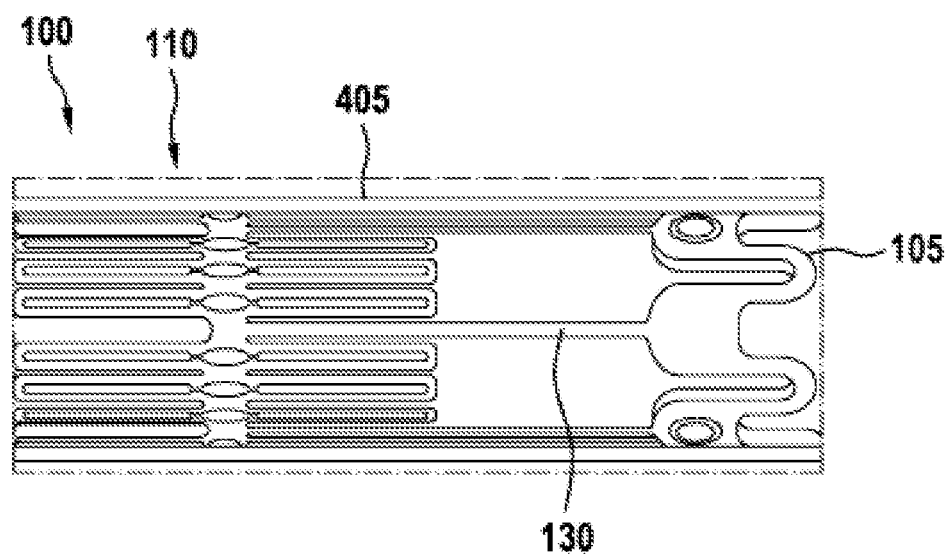
Figure 18C:
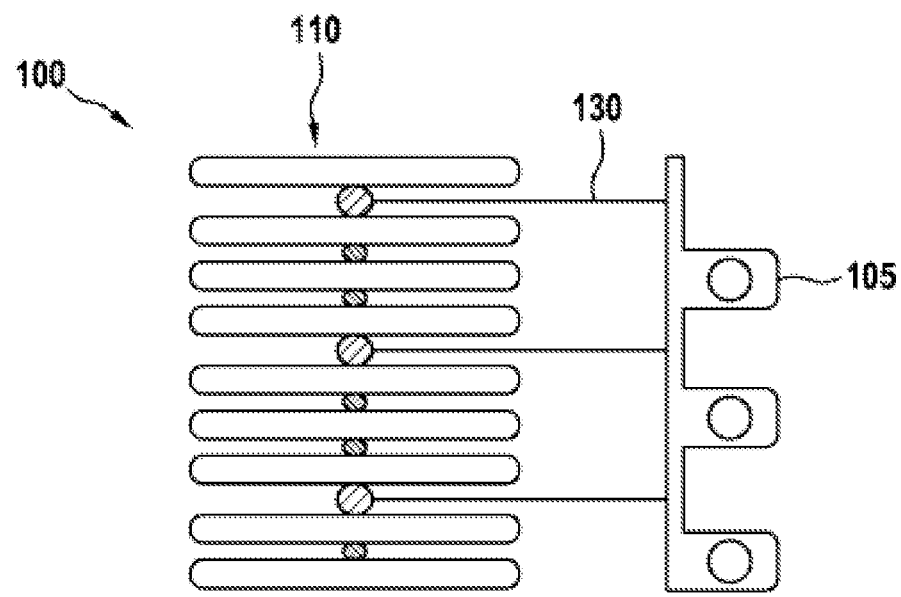
Figure 19A:
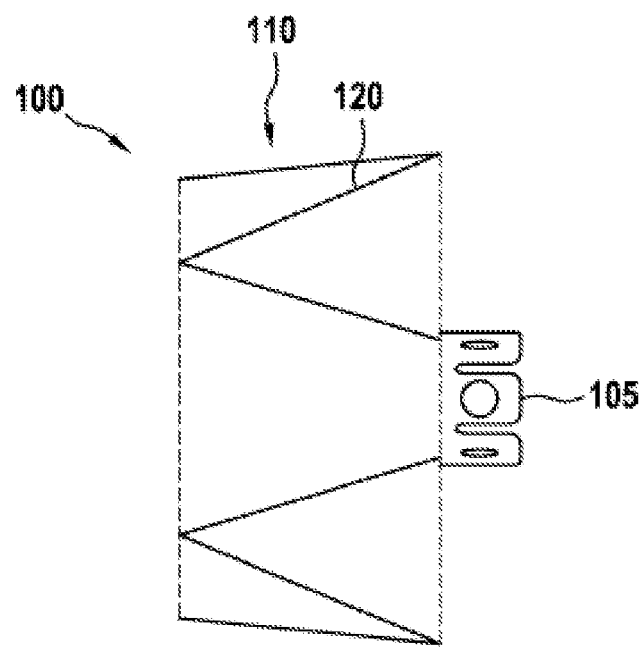
FIG. 19a to 19c a schematic illustration of an apparatus for anchoring a cardiac support system in a blood vessel according to a design example.
Figure 19B:
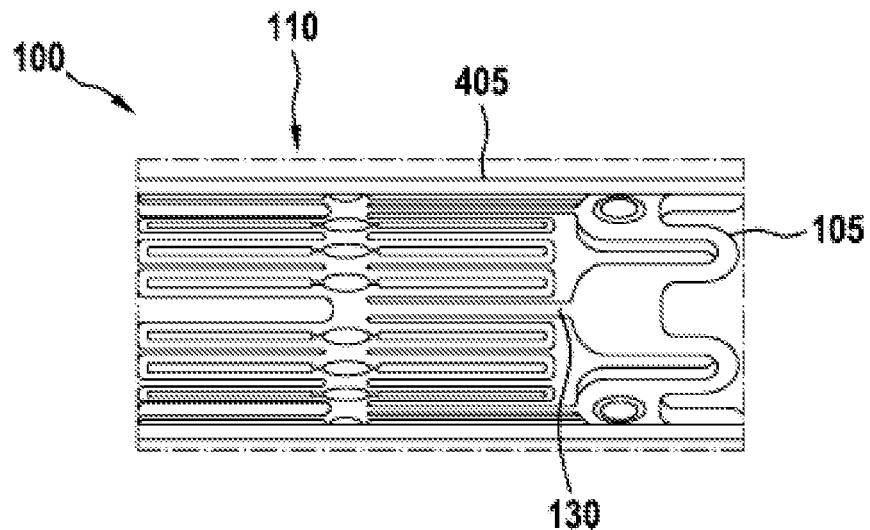
Figure 19C:
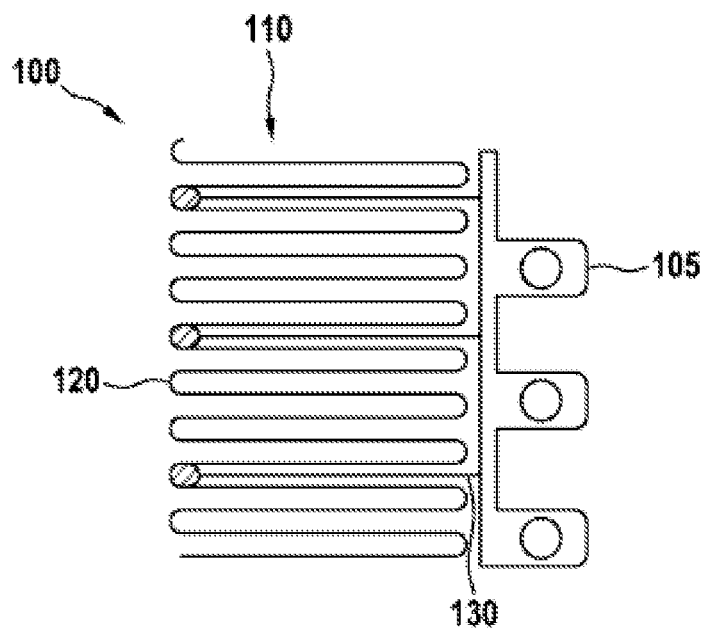

FIGS. 18a to 18c each show a schematic illustration of an apparatus 100 for anchoring a cardiac support system in a blood vessel according to a design example, whereby each figure shows a different situation for the apparatus 100. FIG. 18a shows a plan view of the unfolded apparatus 100, as already described with reference to FIG. 1. FIG. 18b shows a section of the apparatus shown in FIG. 18a in the sleeve 405 in the insertion state, as already described with reference to FIG. 4. FIG. 18c shows a side view of the apparatus 100. The situations shown here are examples of the space required by the apparatus 100 in the insertion state depending on the configuration of the apparatus 100. The following FIGS. 19a to 19c show the situations described here according to an alternative configuration of the crown 110 of the apparatus 100 according to a design example.

FIG. 18a shows a side view of the apparatus 100 according to a design example. The apparatus 100 comprises the fixing means 105, the connection means 115 and the crown 110, whereby the crown 110 is made of a plurality of unfolding elements 120 coupled to one another. Each of the unfolding elements 120 comprises two unfolding rods connected at their ends, which are rhomb-shaped in the unfolding state shown here. The connection means 115 consists of four flexure struts 130, wherein a first end of each flexure strut 130 is fastened to the fixing means 105 and wherein a second end of each flexure strut 130 is fastened to a connection between two adjacent unfolding elements 120.

FIG. 18b shows the apparatus 100 described in FIG. 18a in the insertion state. The crown 110 here is folded for insertion and inserted into the sleeve 405. Due to the described configuration of the crown 110 and the type of fastening of the flexure struts 130, the apparatus 100, also referred to as the anchor, has a comparatively high axial space requirement, for example in comparison to the design example of the apparatus 100 shown in FIG. 19b. According to this design example, the flexure struts 130 are not completely folded in under or between the unfolding elements of the crown 110; rather, they require a certain amount of axial space in the insertion state, which is shown in this figure by the gap between the loaded crown 110 and the fixing means 105.

FIG. 18c schematically shows an illustration of the apparatus 100 in the finished state. The apparatus 100 accordingly does not have the cylindrical shape of the insertion state or the unfolded shape of the anchoring state. The finished state shown here shows an example of the space required by the connection and shape of the crown 110 and the flexure struts 130 of the connection means.

FIG. 19a to 19c each show a schematic illustration of an apparatus 100 for anchoring a cardiac support system in a blood vessel according to a design example. The situations shown in FIG. 19a to 19c each show the apparatus 100 as it is described with reference to FIG. 19a. Shown is a configuration of the crown 110 and the connection means 115, with which the apparatus 100 in the loaded state, as in the folded state corresponding to the insertion state, has a comparatively low axial space requirement. This can be advantageous, for example, if the apparatus is used in conjunction with a cardiac support system, for which additional installation space in this region is advantageous, for example for operating a motor of a heart pump. The saving of axial space can be achieved by a modified geometry of the crown 110 and the connection means 115. The shape of the crown 110, the fastening of the flexure struts 130, as well as the long flexure struts 130 and their change in direction can largely prevent the anchor, i.e. the apparatus 100, from taking up unnecessary installation space during loading. According to the design example shown here, the crown 110 furthermore unfolds at the place at which it is also located in the loaded state.

FIG. 19a shows the apparatus 100 in side view in the unfolded state, whereby the apparatus 100 according to this design example has a low axial space requirement. The crown 110 consists of the at least one unfolding element having a plurality of loops disposed in a meandering manner, as shown in FIG. 19c. The crown 110 is fastened to the fixing means 105.

FIG. 19b shows the apparatus 100 described in FIG. 19a in the insertion state. The crown 110 here is crimped for insertion and inserted into the sleeve 405. Due to the configuration of the crown 110 and the type of fastening of the flexure struts 130, the apparatus 100, also referred to as the anchor, has a comparatively low axial space requirement, for example in comparison to the design example of the apparatus 100 shown in FIG. 18b. According to this design example, the flexure struts 130 are folded in between the unfolding elements of the crown 110; they require only a small amount of axial space in the insertion state, which is shown in this figure by the small gap between the crimped crown 110 and the fixing means 105.

FIG. 19c schematically shows an illustration of the apparatus 100 in the finished state as a further situation. This figure clearly shows the described configurations of the unfolding element 120 with a plurality of meander-like loops and the described connection of the flexure struts 130 to the crown 110. The crown 110 can thus be made of only one single unfolding element 120. The flexure struts 130 of the connection means are disposed inside the meander-like loops, whereby a first end of each flexure strut 130 is fastened to the fixing means 105 and whereby a second end of the flexure strut 130 is fastened to an end of the crown 110 facing away from the fixing means 105. This connection of the flexure struts 130 to the crown 110 is particularly advantageous in terms of the axial space requirement of the apparatus 100 in the insertion state, as shown in the previous situation of the apparatus 100 in FIG. 19b.

Figure 20:
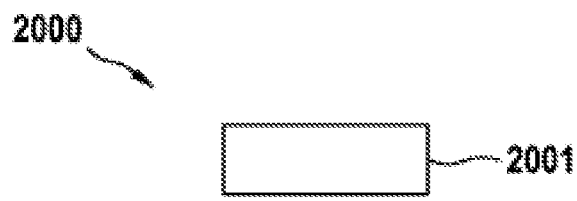
FIG. 20 a flow diagram of a method for operating an apparatus for anchoring a cardiac support system in a blood vessel according to a design example.

FIG. 20 shows a flow diagram of a method 2000 for operating an apparatus for anchoring a cardiac support system in a blood vessel according to a design example. The method 2000 comprises at least one step 2001 of unfolding the unfolding element of the crown of the apparatus during the transition from the insertion state into the anchoring state to increase the diameter of the crown.

Figure 21:
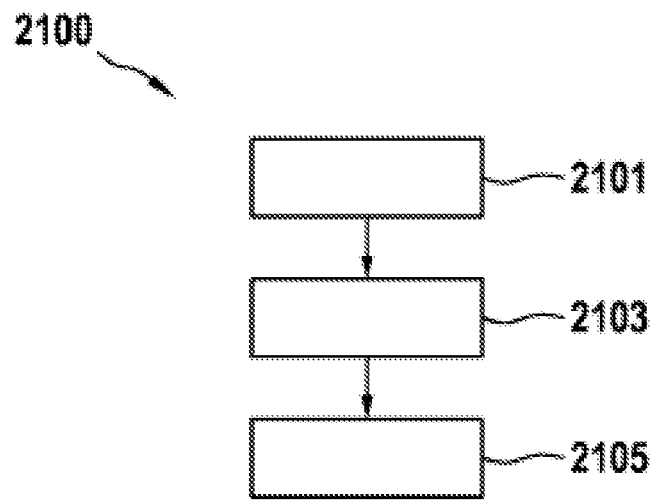
FIG. 21 a flow diagram of a production method for producing an apparatus for anchoring a cardiac support system in a blood vessel according to a design example.

FIG. 21 shows a flow diagram of a production method 2100 for producing an apparatus for anchoring a cardiac support system in a blood vessel according to a design example. The apparatus can assume an insertion state for inserting the cardiac support system into the blood vessel, and the apparatus can assume an anchoring state for anchoring the cardiac support system in the blood vessel. The production method 2100 of the apparatus comprises at least one step 2101 for providing, one step 2103 for forming and one step 2105 for heat treating. In the providing step 2101, a semi-finished product made of a shape memory material is provided. In the forming step 2103, a fixing means for fixing the apparatus to the cardiac support system is formed. The step also includes forming a crown from at least one unfolding element, whereby the unfolding element is designed to unfold during a transition from the insertion state into the anchoring state in order to increase the diameter of the crown to anchor the apparatus in the blood vessel. A connection means is furthermore configured to connect the crown to the connection means. The fixing means, the crown and the connection means are formed from the semi-finished product provided in Step 2101. In the heat-treating step 2105, the fixing means, the crown and the connection means are heat-treated to emboss the shape of the anchoring state.

If a design example includes an "and/or" conjunction between a first feature and a second feature, this should be read to mean that the design example according to one embodiment comprises both the first feature and the second feature and, according to another embodiment, comprises either only the first feature or only the second feature.

In summary, the following preferred features of the invention should in particular be noted: An apparatus 100 for anchoring a cardiac support system in a blood vessel can assume an insertion state for inserting the cardiac support system into the blood vessel and an anchoring state in order to anchoring state the cardiac support system into the blood vessel. The apparatus 100 comprises at least one fixing means 105 for fixing the apparatus 100 to the cardiac support system 205, a crown 110 and a connection means 115. The crown 110 consists of at least one unfolding element 120. The unfolding element 120 is designed to unfold during a transition from the insertion state into the anchoring state in order to increase the diameter of the crown 110 to anchor the apparatus 100 in the blood vessel. The connection means 115 is designed to connect the crown 110 to the fixing means 105.

The invention in particular relates to the aspects specified in the following clauses:

1. Apparatus (100) for anchoring a cardiac support system (205) in a blood vessel, wherein the apparatus (100) can assume an insertion state for inserting the cardiac support system (205) into the blood vessel, and an anchoring state for anchoring the cardiac support system (205) in the blood vessel, and wherein the apparatus (100) has the following features:
   a fixing means (105) for fixing the apparatus (100) to the cardiac support system (205);

a crown (110) that consists of at least one unfolding element (120), wherein the unfolding element (120) is designed to unfold during a transition from the insertion state into the anchoring state in order to increase the diameter of the crown (110) to anchor the apparatus (100) in the blood vessel; and
a connection means (115) which is configured to connect the crown (110) to the fixing means (105).

2. Apparatus (100) according to Clause 1, wherein at least the unfolding element (120) is made of a shape memory material.

3. Apparatus (100) according to any one of the preceding clauses, having an arching device (210) having at least one foot (215), wherein the arching device (210) is designed to unfold during the transition from the insertion state into the anchoring state for positioning the at least one foot (215) in the blood vessel, and wherein the arching device (210) is connected to the crown (110) or wherein the arching device (210) comprises an arch fixing device (305) for fixing the arching device (210) to the cardiac support system (205).

4. Apparatus (100) according to Clause 3, wherein the arching device (210) comprises three feet (215), in particular wherein, for positioning the feet (215), said feet (215) are formed in a respective cusp of a heart valve.

5. Apparatus (100) according to any one of the preceding clauses, wherein the apparatus (100) is cylindrical in the insertion state.

6. Apparatus (100) according to any one of the preceding clauses, wherein the unfolding element (120) has an inclined position relative to the longitudinal axis of the apparatus (100) in the anchoring state.

7. Apparatus (100) according to any one of the preceding clauses, wherein the crown (110) comprises a plurality of unfolding elements (120) coupled to one another, wherein each of the unfolding elements (120) comprises two unfolding rods (125) connected at their ends, wherein the distance between the two unfolding rods (125) is smaller in the insertion state than in the anchoring state.

8. Apparatus (100) according to any one of Clauses 1 to 6, wherein the unfolding element (120) comprises a plurality of loops arranged in a meandering manner, wherein the distance between the loops is smaller in the insertion state than in the anchoring state.

9. Apparatus (100) according to any one of the preceding clauses, wherein the connection means (115) comprises at least one flexure strut (130), wherein the flexure strut (130) is designed to open during the transition from the insertion state into the anchoring state to allow the crown (110) to unfold.

10. Apparatus (100) according to Clause 9, wherein a first end of the flexure strut (130) is fastened to the fixing means (105) and wherein a second end of the flexure strut (130) is fastened to a connection between two adjacent unfolding elements (120) or to an end of the crown (110) facing away from the fixing means (105).

11. Apparatus (100) according to any one of the preceding clauses, wherein the fixing means (105) is designed to fix the apparatus (100) in a form-locking and/or force-locking manner to the cardiac support system (205).

12. Apparatus (100) according to any one of the preceding clauses with a sleeve (405), wherein the sleeve (405) is movable relative to the crown (110) and wherein the sleeve (405) is designed to enclose at least the crown (110) in the insertion state and to release at least the crown to initiate the transition into the anchoring state.

13. Method (2000) for operating an apparatus (100) according to any one of the preceding clauses, wherein the method (2000) comprises at least the following step:
unfolding (2001) the unfolding element (120) of the crown (110) of the apparatus (100) during the transition from the insertion state into the anchoring state to increase the diameter of the crown (110).

14. Production method (2100) for producing an apparatus (100) for anchoring a cardiac support system (205) in a blood vessel, wherein the apparatus (100) can assume an insertion state for inserting the cardiac support system (205) into the blood vessel, and wherein the apparatus (100) can assume an anchoring state for anchoring the cardiac support system (205) in the blood vessel, wherein the production method comprises at least the following step:
providing (2101) a semi-finished product made of a shape memory material;
forming (2103) a fixing means (105) for fixing the apparatus (100) to the cardiac support system (205) and forming a crown (110) from at least one unfolding element (120), wherein the unfolding element (120) is configured to unfold during a transition from the insertion state into the anchoring state to increase the diameter of the crown (110) in order to anchor the apparatus (100) in the blood vessel, and forming a connection means (115), that is shaped to connect the crown (110) to the connection means, wherein the fixing means, the crown (110) and the connection means (115) are made of the semi-finished product; and heat treating (2105) the fixing means, the crown (110) and the connection means (115) in order to emboss the shape of the anchoring state.

15. Cardiac support system (205) having an apparatus (100) according to any one of the preceding clauses.

The invention claimed is:

1. An apparatus for anchoring a cardiac support system in a blood vessel, the apparatus comprising:
a fixing component configured to fix to the cardiac support system;
a ring-shaped crown, wherein a diameter of the ring-shaped crown is configured to increase during a transition of the apparatus from an insertion state into an anchoring state so as to anchor the cardiac support system in the blood vessel, wherein the apparatus is configured to assume the insertion state for inserting the cardiac support system into the blood vessel and to assume the anchoring state for anchoring the cardiac support system in the blood vessel;
a sleeve being movably displaceable relative to the crown during the transition from the insertion state into the anchoring state so as to allow the crown to unfold; and
a connection component configured to connect the crown to the fixing component, the connection component comprising a plurality of flexure struts configured to unfold in response to displacement of the sleeve, wherein each flexure strut of the plurality of flexure struts comprises a first end coupled to the fixing component,
wherein the ring-shaped crown comprises a plurality of unfolding elements configured to unfold during the transition of the apparatus from the insertion state into the anchoring state so as to increase the diameter of the crown, wherein each unfolding element comprises two unfolding rods connected to one another at their ends, wherein the plurality of unfolding elements connect to one another along a circular path, wherein a central section of each unfolding rod of each unfolding element is connected at a connection point to a central section of an adjacent unfolding rod of an adjacent unfolding element, wherein each unfolding rod is disposed closer to each adjacent unfolding rod in the insertion state than in the anchoring state, wherein each of the plurality of flexure struts comprises a second end connected to the connection point of two unfolding rods of adjacent unfolding elements or to a connection at the ends of two unfolding rods of one of the unfolding elements at an end of the crown opposite the fixing component, and wherein the sleeve is configured to enclose the crown in the insertion state and is configured to release the crown so as to initiate the transition from the insertion state into the anchoring state.

2. The apparatus according to claim 1, wherein the unfolding elements are made of a shape memory material.

3. The apparatus according to claim 1, further comprising an arching device comprising at least one foot, wherein the arching device is configured to unfold during the transition from the insertion state into the anchoring state so as to position the at least one foot in the blood vessel, and wherein the arching device is connected to the crown or the arching device comprises an arch fixing device for fixing the arching device to the cardiac support system.

4. The apparatus according to claim 3, wherein the at least one foot comprises three feet, wherein each of the three feet are configured to be positioned in a cusp of a heart valve.

5. The apparatus according to claim 1, wherein the apparatus is cylindrical in the insertion state.

6. The apparatus according to claim 1, wherein the crown and the fixing component extend along a longitudinal axis, and wherein each of the plurality of unfolding elements is configured to be positioned in an inclined position relative to the longitudinal axis of the apparatus in the anchoring state.

7. The apparatus according to claim 1, wherein the fixing component is configured to fix the apparatus to the cardiac support system in a form-locking and/or force-locking manner.

8. A method for producing an apparatus for anchoring a cardiac support system in a blood vessel, the method comprising:

providing a semi-finished product made of a shape memory material;

forming a fixing component, a ring-shaped crown and a connection component from the semi-finished product; and heat treating the fixing component, the crown and the connection component in order to emboss a shape of the anchoring state;

wherein the fixing component is configured to fix to the cardiac support system, wherein a diameter of the ring-shaped crown is configured to increase during a transition of the apparatus from an insertion state into an anchoring state so as to anchor the cardiac support system in the blood vessel, wherein the apparatus is configured to assume the insertion state for inserting the cardiac support system into the blood vessel and to assume the anchoring state for anchoring the cardiac support system in the blood vessel, wherein the apparatus further comprises a sleeve being movably displaceable relative to the crown during the transition from the insertion state into the anchoring state so as to allow the crown to unfold, wherein the connection component is configured to connect the crown to the fixing component, the connection component comprising a plurality of flexure struts configured to unfold in response to displacement of the sleeve, wherein each flexure strut of the plurality of flexure struts comprises a first end coupled to the fixing component, wherein the ring-shaped crown comprises a plurality of unfolding elements configured to unfold during the transition of the apparatus from the insertion state into the anchoring state so as to increase the diameter of the crown, wherein each unfolding element comprises two unfolding rods connected to one another at their ends, wherein the plurality of unfolding elements connect to one another along a circular path, wherein a central section of each unfolding rod of each unfolding element is connected at a connection point to a central section of an adjacent unfolding rod of an adjacent unfolding element, wherein each unfolding rod is disposed closer to each adjacent unfolding rod in the insertion state than in the anchoring state, wherein each of the plurality of flexure struts comprises a second end connected to the connection point of two unfolding rods of adjacent unfolding elements or to a connection at the ends of two unfolding rods of one of the unfolding elements at an end of the crown opposite the fixing component, and wherein the sleeve is configured to enclose the crown in the insertion state and is configured to release the crown so as to initiate the transition from the insertion state into the anchoring state.

9. The method according to claim 8, wherein the apparatus further comprises an arching device comprising at least one foot, wherein the arching device is configured to unfold during the transition from the insertion state into the anchoring state so as to position the at least one foot in the blood vessel, and wherein the arching device is connected to the crown or the arching device comprises an arch fixing device for fixing the arching device to the cardiac support system.

10. The method according to claim 8, wherein the fixing component is configured to fix the apparatus to the cardiac support system in a form-locking and/or force-locking manner.

* * * * *